(12) United States Patent
Matsuzaki et al.

(10) Patent No.: US 9,080,966 B2
(45) Date of Patent: Jul. 14, 2015

(54) DETECTION DEVICE, INFORMATION REPRODUCTION DEVICE, DRIVE DEVICE, SENSOR, AND DETECTION METHOD

(71) Applicant: Panasonic Corporation, Osaka (JP)

(72) Inventors: Keiichi Matsuzaki, Kyoto (JP); Kousei Sano, Osaka (JP); Teruhiro Shiono, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 14/128,875

(22) PCT Filed: Oct. 16, 2012

(86) PCT No.: PCT/JP2012/006621
§ 371 (c)(1),
(2) Date: Dec. 23, 2013

(87) PCT Pub. No.: WO2013/057934
PCT Pub. Date: Apr. 25, 2013

(65) Prior Publication Data
US 2014/0146321 A1 May 29, 2014

(30) Foreign Application Priority Data
Oct. 21, 2011 (JP) ................................ 2011-231392

(51) Int. Cl.
*G01N 21/55* (2014.01)
*G01N 21/41* (2006.01)
(Continued)

(52) U.S. Cl.
CPC ............... *G01N 21/41* (2013.01); *G01N 21/45* (2013.01); *G01N 21/554* (2013.01); *G11B 7/1381* (2013.01); *G11B 7/1384* (2013.01);
(Continued)

(58) Field of Classification Search
USPC .......................... 356/445, 448, 326, 300, 71; 369/112.01, 100; 359/486.01, 486.02; 385/12
See application file for complete search history.

(56) References Cited
U.S. PATENT DOCUMENTS

2002/0009812 A1* 1/2002 Miura et al. .................. 436/518
2010/0039917 A1* 2/2010 Ide ................................ 369/100
(Continued)

FOREIGN PATENT DOCUMENTS

JP 2001-41881 2/2001
JP 2002-8235 1/2002
(Continued)

OTHER PUBLICATIONS

International Search Report issued Feb. 5, 2013 in International (PCT) Application No. PCT/JP2012/006621.
(Continued)

*Primary Examiner* — Tri T Ton
(74) *Attorney, Agent, or Firm* — Wenderoth, Lind & Ponack, L.L.P.

(57) ABSTRACT

The present application discloses a detection device including a light source configured to emit emission light, a scattering substance situated near a target object and configured to generate plasmon resonance between the scattering substance and the target object, a light guide portion configured to guide the emission light to the scattering substance and cause first reflected light, which is reflected from the scattering substance, and a detector configured to detect a state in phase of the first reflected light.

12 Claims, 20 Drawing Sheets

(51) Int. Cl.
G01N 21/552 (2014.01)
G11B 7/1381 (2012.01)
G11B 7/1387 (2012.01)
G01N 21/45 (2006.01)
G11B 7/1384 (2012.01)
G11B 7/1374 (2012.01)
G11B 7/1372 (2012.01)

(52) U.S. Cl.
CPC ............ *G11B 7/1387* (2013.01); *G11B 7/1374* (2013.01); *G11B 2007/13727* (2013.01)

(56) References Cited

U.S. PATENT DOCUMENTS

2010/0053608 A1* 3/2010 Lee ............................... 356/326

2010/0054105 A1 3/2010 Handa

FOREIGN PATENT DOCUMENTS

| JP | 2003-329580 | 11/2003 |
|----|-------------|---------|
| JP | 2006-323989 | 11/2006 |
| JP | 2010-54915  | 3/2010  |
| JP | 2010-129166 | 6/2010  |
| JP | 2010-135020 | 6/2010  |

OTHER PUBLICATIONS

Hideharu Mikami et al., "Amplification of Optical Disc Readout Signals by Homodyne Detection", Technical Journal of the Institute of Image Information and Television Engineers 33(1), Jan. 15, 2009, pp. 35-40.

* cited by examiner

DETECTION DEVICE, INFORMATION REPRODUCTION DEVICE, DRIVE DEVICE, SENSOR, AND DETECTION METHOD

TECHNICAL FIELD

The present invention relates to technologies which use plasmon resonance to detect various characteristics such as physical properties and shapes.

BACKGROUND ART

Plasmon is a vibrational quantum of free electrons in materials such as metal. For example, when nano-scale fine metal (metal nanostructure) is irradiated with light, collective oscillation of the free electrons happens to the metal due to the light. Consequently, the plasmon is excited.

As a result of the excited plasmon, an electromagnetic field with locally high intensity is generated. Energy of the resultant electromagnetic field from the excitation of plasmon may be potentially used for various purposes.

Technologies to optically record information at very high density are known as the potential usage (c.f. Patent Document 1). As described above, light entering a scattering substance excites the localized plasmon. The excitation of the localized plasmon locally intensifies an optical electric field near the scattering substance. Light near the scattering substance is used to record information in a minute area in the order of nanometers outside the diffraction limit.

FIG. 26 is a schematic view of a conventional optical pickup device 900 disclosed in Patent Document 1. The conventional optical pickup device 900 is described with reference to FIG. 26.

The optical pickup device 900 uses plasmon to record or reproduce information on or from a recording medium 910. The optical pickup device 900 includes a laser beam source 920, a mirror 930, a lens 940, a substrate 950 and a scattering substance 960. The laser beam source 920 emits a laser beam LB toward the mirror 930. The mirror 930 reflects the laser beam LB toward the lens 940. The lens 940 focuses the laser beam LB toward the substrate 950.

The substrate 950 is formed from a transparent material to the laser beam LB. The substrate 950 includes a first facing surface 951, which faces the lens 940, and a second facing surface 952, which faces the recording medium 910. The scattering substance 960 is formed on the second facing surface 952. The laser beam LB passing through the lens 940 goes through the first facing surface 951, and then is focused on the scattering substance 960.

The substrate 950 moves above the recording medium 910. The scattering substance 960 is embedded in the second facing surface 952. Consequently, the scattering substance 960 does not interfere with the movement of the substrate 950 above the recording medium 910. According to Patent Document 1, the second facing surface 952 of the substrate 950 is provided with a cylindrical hole, which is approximately 50 nm in diameter and approximately 100 nm in depth. The scattering substance 960 is gold embedded in the cylindrical hole.

The optical pickup device 900 includes a position adjustment mechanism (not shown) to get the lens 940 closer to and away from the substrate 950. The position adjustment mechanism slightly moves the lens 940 vertically. The position adjustment mechanism adjusts and fixes a position of the lens 940 so that the focal point of the laser beam LB coincides with the center of the scattering substance 960.

Localized plasmon is excited around the scattering substance 960 under appropriate positional adjustment to the lens 940 if the laser beam LB enters the scattering substance 960. Consequently, the optical electric field is intensified near the scattering substance 960.

According to Patent Document 1, the scattering substance 960 is a cylindrical minute metal. The bottom surface of the scattering substance 960 is substantially flush with the second facing surface 952, which faces the recording medium 910. Accordingly, the intensified optical electric field covers in an area, which substantially corresponds to the bottom surface of the scattering substance 960 (i.e. circular area which is approximately 50 nm in diameter).

The optical pickup device 900 may be mounted on a recording device or a reproduction device. The recording or reproduction device may have functions for controlling a distance between the scattering substance 960 and the recording medium 910. When the scattering substance 960 gets closer to be a predetermined distance from the recording medium 910, information (hereinafter referred to as "spot information") is recorded in an area corresponding to the spot diameter of the area of the intensified optical electric field.

Less intensified light than the light used for the recording operation is utilized in order to reproduce the spot information recorded on the recording medium 910. The optical pickup device 900 detects the reflected light, which is reflected from the scattering substance 960, or the transmitted light, which is transmitted through the scattering substance 960. Consequently, information written in a minute area below the diffraction limit is reproduced.

The scattering substance 960, which is used in the conventional optical pickup device 900 shown in FIG. 26, is sized to be not greater than a wavelength of the laser beam LB, in order to satisfy conditions for generating localized plasmon resonance Since the size of the scattering substance 960 is several hundred nm or less, the reproduction light, which is used for reproducing the recorded information (reflected light which is reflected from the scattering substance 960 or transmitted light which is transmitted through the scattering substance 960), is very weak. Accordingly, the conventional optical pickup device 900 needs a very sensitive photoelectric detector in order to detect the weak reproduction light.

Optical devices such as photo-multipliers and avalanche photodiodes (APD) are known as highly sensitive photoelectric detectors. With regard to photo-multipliers, an oversized element may be a problem. Accordingly, it is physically difficult to manufacture a practical optical pickup device by using a photo-multiplier. In addition, since elements of a photo-multiplier are expensive, it is also difficult to manufacture a practical optical pickup device in terms of manufacturing costs. If an avalanche photodiode is used, a temperature control system to reduce temperature drift of elements and a control circuit to handle high voltages are required. Consequently, the use of an avalanche photodiode complicates a reproduction light detection system.

As described above, the lens 940 focuses light toward the scattering substance 960 to cause a light focusing spot. Due to the diffraction limit of light, the lens 940 may not form a light focusing spot smaller than the wavelength of the light in principle. Accordingly, the light focusing spot may be larger than the scattering substance 960.

As a result of the larger light focusing spot than the scattering substance 960, even when the lens 940 focuses light on the scattering substance 960, there may be light components beyond the scattering substance 960. The light components beyond the scattering substance 960 are scattered or reflected around the scattering substance. Accordingly, the light components beyond the scattering substance 960 may be superimposed as noise light on the reflected light from the scattering substance 960, which is used for signal reproduction. As described above, since noise light is superimposed on the very weak reproduction light, it is very difficult to obtain reproduction signals excellent in a signal/noise ratio (SN ratio), by means of the conventional optical pickup device 900 which utilizes plasmon.

The aforementioned problems are common among various devices which utilize plasmon resonance.

Patent Document 1: JP 2002-8235 A

SUMMARY OF THE INVENTION

The present invention provides technologies which allow detection of a state of a target object with little influence from noise.

A detection device according to one aspect of the present invention includes a light source configured to emit emission light, a scattering substance situated near a target object and configured to cause plasmon resonance between the scattering substance and the target object, a light guide portion configured to guide the emission light to the scattering substance and cause first reflected light which is reflected from the scattering substance, and a detector configured to detect a state in phase of the first reflected light.

A information reproduction device according to another aspect of the present invention includes the aforementioned detection device. The information reproduction device uses the detection device to reproduce information recorded on the information recording medium and identify whether a structure is in a recorded state or an unrecorded state.

A drive device according to yet another aspect of the present invention includes the aforementioned detection device, a driver configured to drive an information recording medium, and a controller configured to control the driver and the detection device in response to an output signal which is output from the detection device.

A sensor according to still another aspect of the present invention includes the aforementioned detection device. The plasmon resonance changes in intensity in response to whether the target object contains a specific material. The detection device detects the state in phase to identify whether the target object contains the specific material.

A sensor according to yet another aspect of the present invention includes the aforementioned detection device. The plasmon resonance changes in intensity in response to a shape of the target object. The detection device detects the state in phase to identify the shape of the target object.

A detection method according to still another aspect of the present invention includes steps of emitting emission light, guiding the emission light to a scattering substance situated near a target object to reflect the emission light from the scattering substance and cause first reflected light, and detecting the state in phase of the first reflected light on the basis of plasmon resonance between the target object and the scattering substance.

The present invention may enable detection of the state of the target object without little influence to noise.

The object, features and advantages of the present invention will become apparent based on the following detailed description and accompanying drawings.

DETAILED DESCRIPTION OF THE INVENTION

Figure 1:
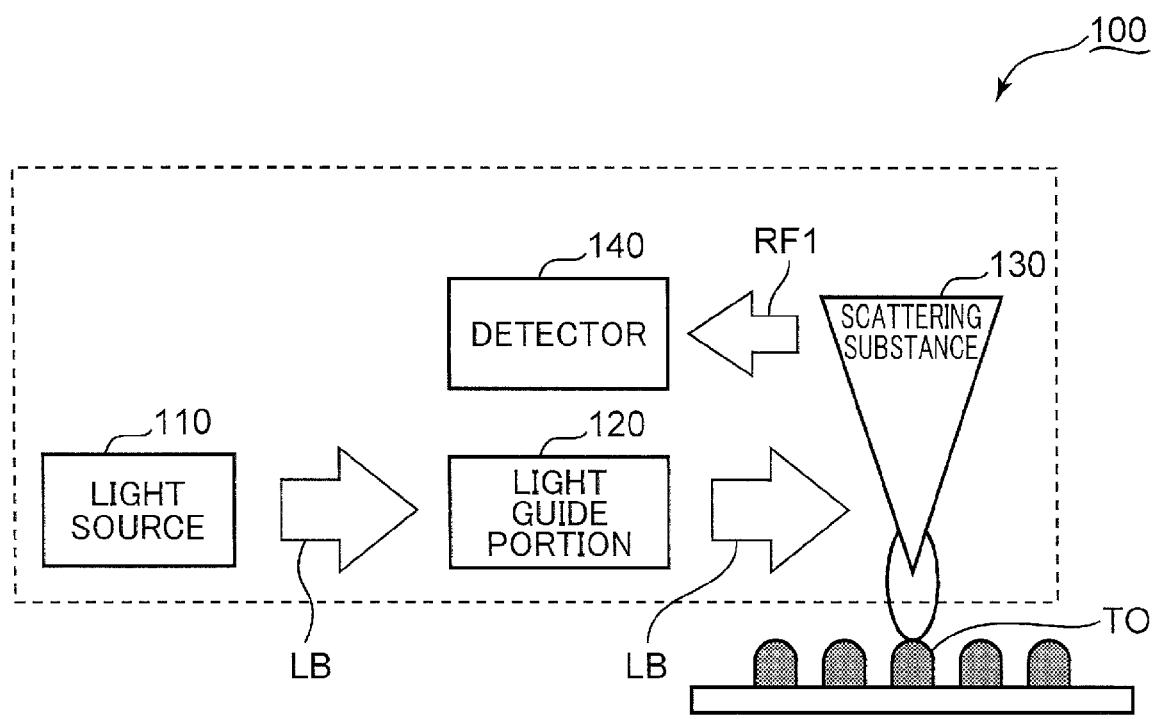
FIG. 1 is a schematic view of a detection device according to the first embodiment.

Various devises which utilize plasmon resonance are described with reference to the drawings. It should be noted that the same reference numerals are assigned to the same components in the following embodiments. In order to clarify concepts of the devices, redundant description is omitted as appropriate. Configurations, arrangements and shapes shown in the drawings as well as descriptions related to the drawings are merely provided for making principles of the embodiments easily understood. Accordingly, the principles of the embodiments are not in any way limited to these.

First Embodiment

Detection Device

FIG. 1 is a schematic view of the detection device 100. The detection device 100 is described with reference to FIG. 1.

The detection device 100 may utilize plasmon resonance generated near a target object TO to detect various characteristics. If the target object TO is a recording medium on which information is recorded, the detection device 100 may detect and reproduce the information from the recording medium. The detection device 100 may be used for inspection of the target object TO. The detection device 100 may be used for detecting whether the target object TO contains specific materials. Alternatively, the detection device 100 may be used for detecting a shape of the target object TO. For example, the detection device 100 may accurately detect geometric characteristics of a surface of the target object TO.

The detection device 100 includes a light source 110, a light guide portion 120, a scattering substance 130, and a detector 140. In this embodiment, the light source 110 emits a laser beam LB. Alternatively, optical elements configured to emit light for generating plasmon resonance between the scattering substance 130 and the target object TO may be used as the light source 110. In this embodiment, the laser beam LB is exemplified as the emission light.

The light source 110 emits the laser beam LB toward the light guide portion 120. The light guide portion 120 guides the laser beam LB to the scattering substance 130. The light guide portion 120 may be an optical system which is formed by using a collimator lens, a mirror or an objective lens unit. Alternatively, the light guide portion 120 may be a waveguide or another optical structure configured to guide the laser beam LB toward the scattering substance 130.

The scattering substance 130 is situated near the target object TO. In this embodiment, a distance between the scattering substance 130 and the target object TO is set so that plasmon resonance is generated between the scattering substance 130 and the target object TO. When the light guide portion 120 guides the laser beam LB to the scattering substance 130, plasmon resonance is generated between the target object TO and the scattering substance 130. The scattering substance 130 reflects the laser beam LB to generate reflected light RF1. In this embodiment, the reflected light RF1 is exemplified as the first reflected light.

The detector 140 receives the reflected light RF1, and detects a state in phase of the reflected light RF1. The detector 140 may detect a change in the phase as the state in phase. Alternatively, the detector 140 may detect a value of the phase, which is greater than or smaller than a predetermined threshold, as the state in phase. The state in phase of the reflected light RF1 changes in response to a change in intensity of the plasmon resonance. The intensity of the plasmon resonance changes in response to a state of the target object TO. Accordingly, the detection device 100 may detect the state in phase of the reflected light RF1 to acquire information about the state of the target object TO.

The detector 140 may include an interference optical system. The interference optical system may separate a part of the laser beam LB emitted from the light source 110 to generate reference light. The interference optical system may cause interference between the reference light and the reflected light RF1 from the scattering substance 130 to generate interfering light.

The detector 140 may include a photo-receiver configured to receive the interfering light. The photo-receiver may detect the interfering light to identify the state in phase of the reflected light RF1. Output signals may be generated and output by the photo-receiver in response to the state in phase of the reflected light RF1. Accordingly, the detection device 100 may detect the interfering light obtained from the interference optical system to acquire information about the state in phase of the reflected light RF1.

If the detector 140 includes the interference optical system and the photo-receiver, the detection device 100 may accurately and easily detect the state in phase of the reflected light RF1 on the basis of a change in intensity of the interfering light.

Second Embodiment

Configuration of Optical Pickup Device

Figure 2:
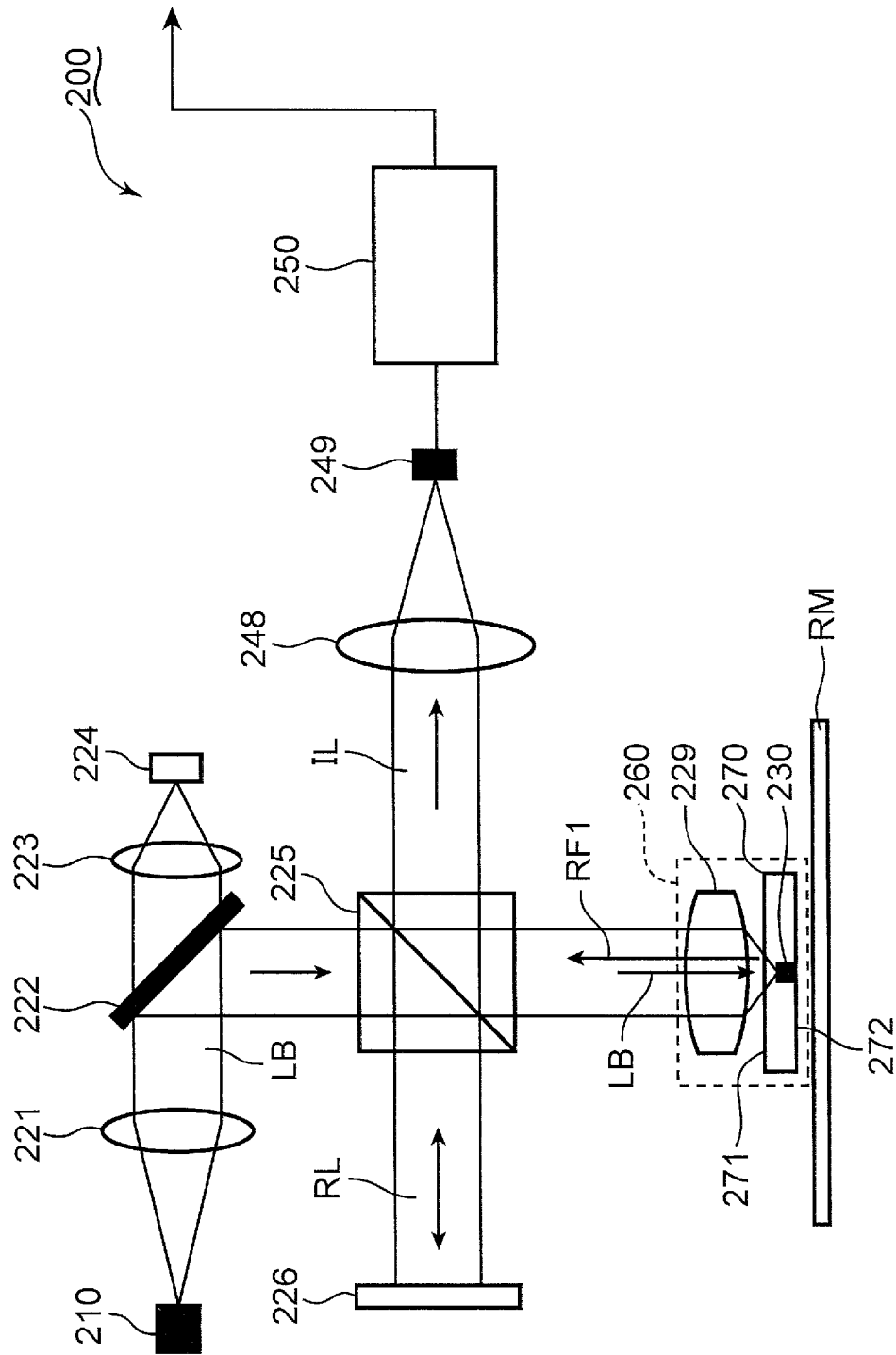
FIG. 2 is a schematic view of an optical pickup device exemplified as a detection device according to the second embodiment.

FIG. 2 is a schematic view of an optical pickup device 200 exemplified as the detection device. The optical pickup device 200 is designed on the basis of the principles of the detection device 100 described in the context of the first embodiment. The optical pickup device 200 is described with reference to FIGS. 1 and 2.

The optical pickup device 200 includes a laser beam source 210, a collimator lens 221, a mirror 222, a condensing lens 223, a light-receiving element 224, a beam splitter 225, a mirror 226, a detection lens 248, a photo-detector 249, a signal processor 250, and an objective lens unit 260. The objective lens unit 260 includes an objective lens 229, a substrate 270, and a scattering substance 230 mounted on the substrate 270. The laser beam source 210 corresponds to the light source 110 described in the context of the first embodiment. The objective lens 229 corresponds to the light guide portion 120 described in the context of the first embodiment. The scattering substance 230 shown in FIG. 2 corresponds to the scattering substance 130 described with reference to FIG. 1. The detection lens 248 and the photo-detector 249 correspond to the detector 140 described in the context of the first embodiment.

In this embodiment, the optical pickup device 200 reproduces information recorded on a recording medium RM. Otherwise, the optical pickup device 200 may optically record information on the recording medium RM. The recording medium RM corresponds to the target object TO described in the context of the first embodiment.

The laser beam source 210 emits the laser beam LB toward the collimator lens 221. In this embodiment, the laser beam LB is exemplified as the emission light.

The collimator lens 221 converts the laser beam LB into collimated light. Subsequently, the laser beam LB travels toward the mirror 222. The mirror 222 reflects a part of the laser beam LB toward the beam splitter 225. The mirror 222 allows passage of the remainder of the laser beam LB. The laser beam LB passing through the mirror 222 is focused on the light-receiving element 224 by the condensing lens 223. The light-receiving element 224 outputs signals in response to the received light. The signals output by the light-receiving element 224 may be used for controlling drive of the optical pickup device 200.

The laser beam LB reflected by the mirror 222 enters the beam splitter 225. The beam splitter 225 reflects a part of the laser beam LB toward the mirror 226 to generate reference light. The beam splitter 225 allows passage of the remaining laser beam LB. In this embodiment, the beam splitter 225 is exemplified as the reference light generator.

In this embodiment, a part of the laser beam LB is used as the reference light. Alternatively, an exclusive light source may be provided to generate the reference light. Accordingly, the reference light generator may be formed as a part of the light guide portion 120 or an optical system different from the light guide portion 120.

The laser beam LB passing through the beam splitter 225 enters the objective lens 229. The substrate 270 includes a first facing surface 271, which faces the objective lens 229, and a second facing surface 272 opposite to the first facing surface 271. The second facing surface 272 faces the recording medium RM. The scattering substance 230 is mounted on the second facing surface 272. The objective lens 229 focuses the laser beam LB toward the scattering substance 230.

The scattering substance 230 may be a metal material such as gold, silver, platinum, aluminum or chromium. Alternatively, the scattering substance 230 may be alloy containing metal materials such as gold, silver, platinum, aluminum or chromium. The scattering substance 230 may be formed from diamond-like carbon, carbon nanotube or other materials capable of collaborating with the recording medium RM to generate plasmon resonance.

In this embodiment, the second facing surface 272 is provided with a hole. The scattering substance 230 is embedded into the hole formed on the second facing surface 272. Consequently, the scattering substance 230 is less likely to come into contact with the recording medium RM during movement of the objective lens unit 260 above the recording medium RM. Accordingly, the scattering substance 230 is less likely to be damaged and separated from the second facing surface 272.

When the scattering substance 230 is irradiated with the laser beam LB, localized plasmon is excited at the scattering substance 230. Consequently, there is an intensified optical electric field near the scattering substance 230.

In this embodiment, a cylindrical object, which is approximately 50 nm in diameter, is used as the scattering substance 230. In this case, an area of the intensified optical electric field becomes a circular area, which is approximately 50 nm in diameter that corresponds to the bottom surface of the cylindrical object.

When the scattering substance 230 gets closer to the recording medium RM until a distance between the scattering substance 230 and the recording medium RM becomes a predetermined value, information is recorded in the circular area of the intensified optical electric field.

(Reproduction Operation of Optical Pickup Device)

The reproduction operation of the optical pickup device 200 is described with reference to FIG. 2.

As described above, the laser beam LB emitted from the laser beam source 210 reaches the scattering substance 230. The scattering substance 230 reflects the laser beam LB to generate the reflected light RF1. The reflected light RF1 travels toward the beam splitter 225 through the objective lens 229. In this embodiment, the reflected light RF1 is exemplified as the first reflected light.

As described above, the beam splitter 225 converts a part of the laser beam LB into the reference light RL. The reference light RL is reflected by the mirror 226, and travels toward the beam splitter 225 once again. The beam splitter 225 allows passage of the reference light RL reflected from the mirror 226 whereas the beam splitter 225 reflects the reflected light RF1 from the scattering substance 230 toward the detection lens 248. Consequently, the reference light RL and the reflected light RF1 are multiplexed between the beam splitter 225 and the detection lens 248 to become interfering light IL. In this embodiment, the mirror 226 and the beam splitter 225 are exemplified as the interference optical system.

The interfering light IL enters the detection lens 248. The detection lens 248 focuses the interfering light IL on the photo-detector 249. The photo-detector 249 generates electrical signals in response to the interfering light IL. In this embodiment, the detection lens 248 and the photo-detector 249 are exemplified as the photo-receiver. The electric signals generated by the photo-detector 249 are exemplified as the output signal.

When the optical pickup device 200 emits the laser beam LB toward the scattering substance 230 and causes the substrate 270 to get closer to the recording medium RM, a recording mark is formed on a surface of the recording medium RM. If the emission of the laser beam from the laser beam source 210 is controlled on the basis of information recorded on the recording medium RM while the recording medium RM rotates, the recording medium RM may have an area, in which the recording mark is formed, and an area, on which the recording mark is not formed. In the following description, a state of the area on which the recording mark is formed is referred to as "recorded state". A state of the area on which the recording mark is not formed is referred to as "unrecorded state".

Generation of the recorded and unrecorded states on the recording medium RM may be dependent on similar principles to practical phase change disks (e.g. DVD or Blu-ray disk). In this embodiment, the recording medium RM includes a phase change film. The phase change film changes between a non-crystalline state (amorphous) and a crystalline state in response to non-irradiation/irradiation of the laser beam LB. In this embodiment, an area of the crystalline state is exemplified as the area of the recorded state whereas an area of the non-crystalline state is exemplified as the area of the unrecorded state. Alternatively, the area of the crystalline state may be exemplified as the area of the unrecorded state whereas the area of the non-crystalline state may be exemplified as the area of the recorded state.

Plasmon resonance generated between the area of the recorded state and the scattering substance 230 is different in intensity from plasmon resonance generated between the area of the unrecorded state and the scattering substance 230. A phase of the reflected light RF1 depends on the intensity of the plasmon resonance. In other words, a change in the intensity of the plasmon resonance appears as a change in the phase of the reflected light RF1. The photo-detector 249 detects the change in the phase of the reflected light RF1 as the change in the intensity of the interfering light IL. The photo-detector 249 outputs electric signals which indicate the intensity change of the interfering light IL. According to the principles of this embodiment, the electric signals may accurately express a distribution of areas of the recorded and unrecorded states in a surface of the recording medium RM. The signal processor 250 uses the electric signals from the photo-detector 249 to execute information reproduction processes.

The signal processor 250 converts the electric signals from the photo-detector 249 into reproduction signals during the reproduction processes. The reproduction signals as digital signals express the information recorded on the recording medium RM.

The various elements shown in FIG. 2 may be formed by using a thin film. With a light focusing circuit, which is configured by integrating elements formed as a thin film and a substrate, a compact design of the optical pickup device 200 described with reference to FIG. 2 is achieved.

(Principles about Phase Change of Reflected Light)

Figure 3:
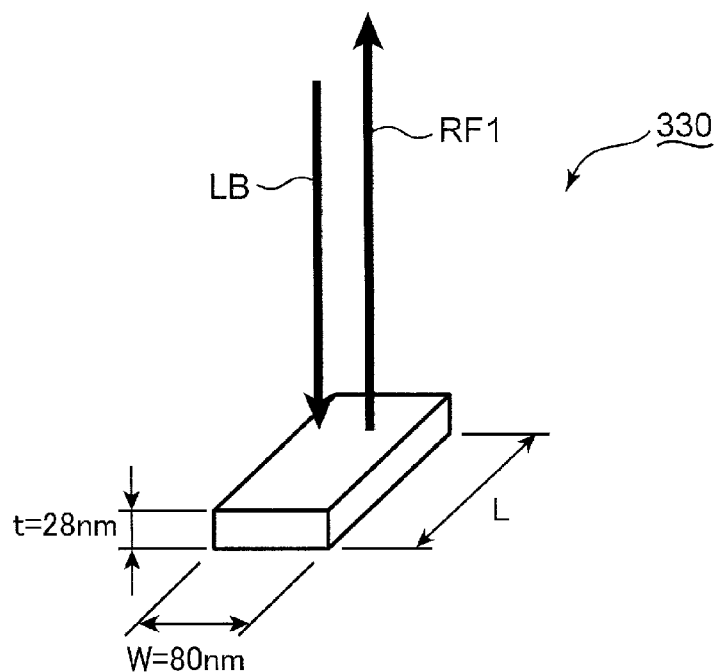
FIG. 3 is a schematic perspective view of an exemplary scattering substance.

FIG. 3 is a schematic perspective view of a scattering substance 330. Description about the scattering substance 330 may be applied to the aforementioned scattering substances 130, 230. The principles about the phase change of the reflected light RF1 is described with reference to FIGS. 1 to 3.

FIG. 3 shows a rectangular scattering substance 330 of a cross section, which is 28 nm in thickness (indicated with the symbol "t" in FIG. 3) and 80 nm in width (indicated with the symbol "w" in FIG. 3). A length of the scattering substance 330 is indicated with the symbol "L". The laser beam LB entering the scattering substance 330 is "780 nm" in wavelength. A polarization direction of the laser beam LB coincides with the direction of the length "L" of the scattering substance 330.

Plasmon light generated at the scattering substance 330 resonates strongly only under satisfaction of specific conditions (hereinafter referred to as "resonance condition"). If the plasmon light is in a resonance state, the optical electric field is locally intensified at a predetermined position near the scattering substance 330. The resonance condition is dependent on a wavelength of the laser beam LB, a polarization state of the laser beam LB, a structure of the scattering substance 330, a complex index of refraction of the scattering substance 330, a substrate (substrate 270 in FIG. 2) to which the scattering substance 330 is mounted, a refractive index of the recording medium (target object TO in FIG. 1, recording medium RM in FIG. 2), and a distance (gap interval) between the recording medium and the scattering substance 330.

Figure 4:
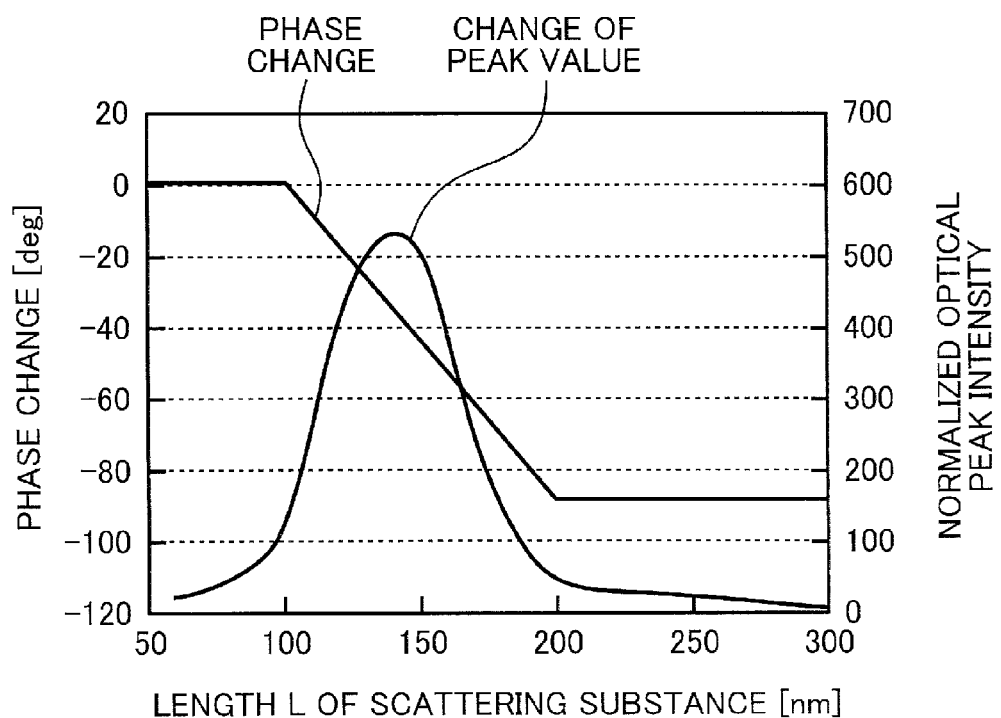
FIG. 4 is a graph showing a phase change of reflected light in response to a change in a length of the scattering substance shown in FIG. 3 and a change in peak value at optical intensity of the scattering substance.

FIG. 4 is a graph showing a phase change of the reflected light RF1 from the laser beam LB (incident light) under a change in the length "L" of the scattering substance 330 among various parameters determining a resonance condition and a change in a peak value of optical intensity at the scattering substance 330. The phase change of the reflected light RF1, and the change in the peak value of the optical intensity over the change in the length "L" of the scattering substance 330 are described with reference to FIGS. 1 to 4.

In FIG. 4, the phase change of the reflected light RF1 is indicated with a broken line. In FIG. 4, the change in the peak value of the optical intensity is indicated with a curve. The peak value shown in FIG. 4 is indicated as the peak intensity which normalizes the peak value of the optical intensity distribution in the scattering substance 330 by using the intensity of the laser beam LB. It should be noted that the peak value shown in FIG. 4 is a result of numeric calculations on the basis of the FDTD method (Finite Difference Time Domain Method). In the case of the scattering substance 330 shown in FIG. 3, the peak of the optical intensity distribution appears near the eight apexes of the scattering substance 330. It should be noted that the FDTD method is used for differentiating the Maxwell's equation to perform numeric calculations of the electromagnetic field distribution. The FDTD method is generally used with a computer for analyzing phenomenon such as plasmon resonance.

With regard to the change in the peak value shown in FIG. 4, when the length "L" of the scattering substance 330 changes, the peak intensity also changes. If the length "L" of the scattering substance 330 is "150 nm", the distribution of the peak intensity reaches the peak. In other words, if the length "L" of the scattering substance 330 is "150 nm", large plasmon resonance is generated at the scattering substance 330 to locally intensify a electromagnetic field distribution.

With regard to the phase change of the reflected light RF1 shown in FIG. 4, the phase of the reflected light RF1 changes considerably under a condition to intensify the plasmon resonance (i.e. when the length "L" of the scattering substance 330 is "150 nm").

As described with reference to FIG. 2, areas of the recorded and unrecorded states are formed on a surface of the recording medium RM. The condition for generating plasmon resonance at the scattering substance 230 and the condition without plasmon resonance at the scattering substance 230 are created on the basis of whether an area near the scattering substance 230 is in the recorded or unrecorded state. The phase of the reflected light RF1 from the scattering substance 230 is changed by whether the plasmon resonance happens to the scattering substance 230.

As described with reference to FIG. 2, the photo-detector 249 may detect the state in phase of the reflected light RF1 from the scattering substance 230 on the basis of an intensity change of the interfering light IL. Consequently, the signal processor 250 may read information recorded on the recording medium RM, and then output the read information as digital signals.

In this embodiment, the intensity of the plasmon resonance generated between the scattering substance 230 and the recording medium RM is changed by whether a predetermined area of the recording medium RM as the target object is in the recorded state (a state in which a recording mark is formed) or in the unrecorded state (a state in which a recording mark is not formed). The detection of the state in phase of the reflected light RF1 from the scattering substance 230 is used for identifying whether a predetermined area of the recording medium RM is in the recorded or unrecorded state.

If the aforementioned detection of the phase of the reflected light RF1 is utilized, a state of a predetermined area of the recording medium RM is detected with high sensitivity and little noise.

The optical pickup device 200 according to this embodiment uses the principles of the detection device 100 described in the context of the first embodiment to reproduce information recorded on the recording medium RM. Since the optical pickup device 200 accurately identifies whether a predetermined area of the recording medium RM is in the recorded or unrecorded state, the optical pickup device 200 may accurately reproduce the information recorded on the recording medium RM.

Third Embodiment

Light Focusing System

In the second embodiment, the objective lens 229 is used as a light focusing system for the scattering substance 230. The objective lens 229 focuses the laser beam LB on the scattering substance 230, which is mounted on the second facing surface 272 of the substrate 270, to generate plasmon light around the scattering substance 230. In this embodiment, a light focusing system, which is used instead of the objective lens 229, is described.

Figure 5:
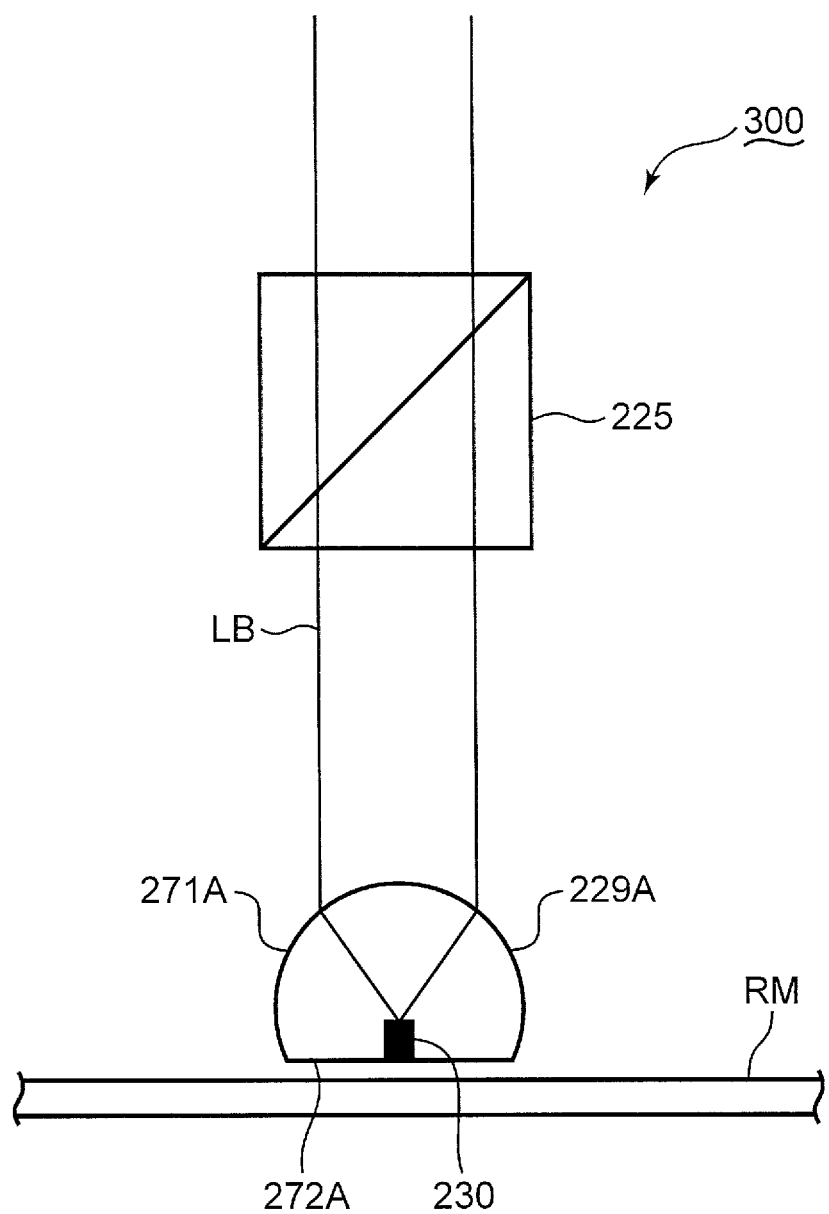
FIG. 5 is a schematic view of a light focusing system exemplified as a light guide portion (the third embodiment).

FIG. 5 is a schematic view of the light focusing system 300, which is used instead of the objective lens 229. The light focusing system 300 is described with reference to FIGS. 2 and 5. It should be noted that the same reference numerals are assigned to the same components as those described in the context of the second embodiment. The description in the second embodiment is applicable to the components, to which the same reference numerals are assigned. The light focusing system 300 may be exemplified as the light guide portion.

FIG. 5 shows a semispherical lens 229A in addition to the beam splitter 225 described in the context of the second embodiment. Like the second embodiment, the beam splitter 225 allows passage of a part of the laser beam LB. The laser beam LB passing through the beam splitter 225 enters the lens 229A.

The lens 229A includes a spherical surface portion 271A, which forms a semispherical profile, and a flat mounting surface 272A facing the recording medium RM. The scattering substance 230 is embedded into the mounting surface 272A. The laser beam LB passing through the beam splitter 225 enters the spherical surface portion 271A. The spherical surface portion 271A refracts the laser beam LB to focus the refracted laser beam LB on the scattering substance 230 embedded into the mounting surface 272A.

In this embodiment, the scattering substance 230 is integrated with the lens 229A. Accordingly, unlike the first embodiment, no positional adjustment is required between a lens element, which has focusing functions, and the scattering substance 230. Accordingly, a design of the light focusing system 300 may be simplified.

Fourth Embodiment

Light Focusing System

In the second embodiment, the objective lens 229 is used as the light focusing system for the scattering substance 230. The objective lens 229 focuses the laser beam LB on the scattering substance 230, which is mounted on the second facing surface 272 of the substrate 270, to generate plasmon light around the scattering substance 230. In this embodiment, a light focusing system, which is used instead of the objective lens 229, is described.

Figure 6:
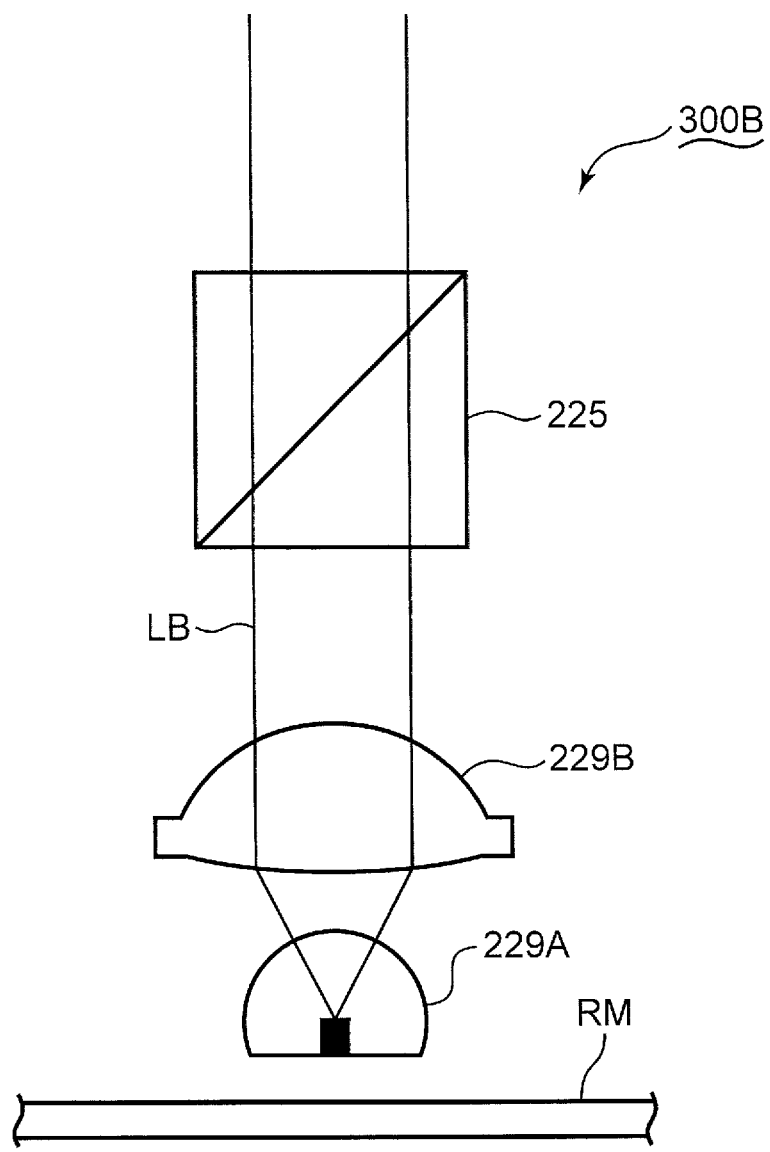
FIG. 6 is a schematic view of another light focusing system exemplified as the light guide portion (the fourth embodiment).

FIG. 6 is a schematic view of the light focusing system 300B, which is used instead of the objective lens 229. The light focusing system 300B is described with reference to FIGS. 2 and 6. It should be noted that the same reference numerals are assigned to the same components as those described in the context of the second and third embodiments. The descriptions in the second and third embodiments are applicable to the components, to which the same reference numerals are assigned. The light focusing system 300B may be exemplified as the light guide portion.

FIG. 6 shows a condensing lens 229B in addition to the beam splitter 225 described in the context of the second embodiment and the semispherical lens 229A described in the context of the third embodiment. The condensing lens 229B is situated between the beam splitter 225 and the lens 229A. The condensing lens 229B and the lens 229A function as a solid immersion lens.

When the refractive index of the semispherical lens 229A is represented with the symbol "n", a light focusing spot created by the condensing lens 229B is reduced to "1/n" in the lens 229A. It should be noted that the lens 229A may have a super-semispherical shape.

When a radius of the super-semispherical lens 229A is represented with the symbol "r", the thickness "LT" of the lens 229A, which is measured from the flat mounting surface 272A, may be expressed by the following formula.

$$LT = r \times \left(1 + \frac{1}{n}\right) \qquad \text{[Formula 1]}$$

Accordingly, if the lens 229A has a super-semispherical shape, the light focusing spot created by the condensing lens 229B is reduced to "1/(n×n)" in the lens 229A.

Since a small light focusing spot reduces stray light, there may be efficient usage of the light. Accordingly, there may be few optical noise components in reproduction signals.

The various light focusing systems 300, 300B are described in the second and third embodiments. The light focusing systems 300, 300B are used for guiding the laser beam LB to the scattering substance 230. An optical waveguide may be used instead of the light focusing systems 300, 300B. If an optical waveguide guides the laser beam LB to the scattering substance 230, and then guides the reflected light RF1 reflected from the scattering substance 230 or the transmitted light passing through the scattering substance 230 to the photo-detector 249, reproduction signals may be appropriately detected on the basis of the principles of the aforementioned various embodiments.

Fifth Embodiment

Scattering Substance

In the second embodiment, the scattering substance 230 is a cylindrical object. In this embodiment, various scattering substances, which are geometrically different from the second embodiment, are explained.

Figure 7:
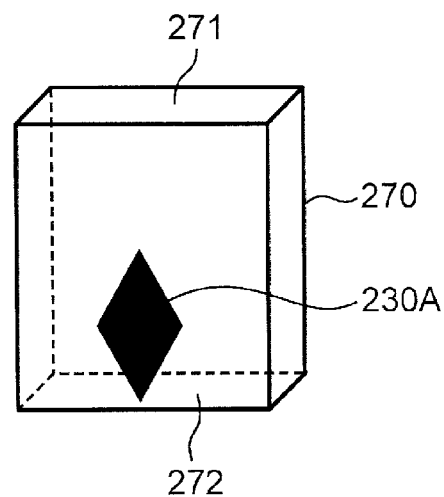
FIG. 7 is a schematic perspective view of an exemplary scattering substance (the fifth embodiment).

FIG. 7 is a schematic perspective view of the scattering substance 230A mounted on the substrate 270. The scattering substance 230A is described with reference to FIGS. 2 and 7. It should be noted that the same reference numerals are assigned to the same components as those described in the context of the second embodiment. The description in the second embodiment is applicable to the components, to which the same reference numerals are assigned.

The scattering substance 230A shown in FIG. 7 has a three-dimensional shape obtained by superimposing a pyramid pointed toward the first facing surface 271 with a pyramid pointed toward the second facing surface 272. The scattering substance 230A has a cross section of a diamond shape or a rectangular shape. Consequently, the scattering substance 230A has a wider reflection area greater than the scattering substance 230 described in the context of the second embodiment does. Accordingly, a light amount of the reflected light RF1 reflected from the scattering substance 230A is relatively increased.

Figure 8:
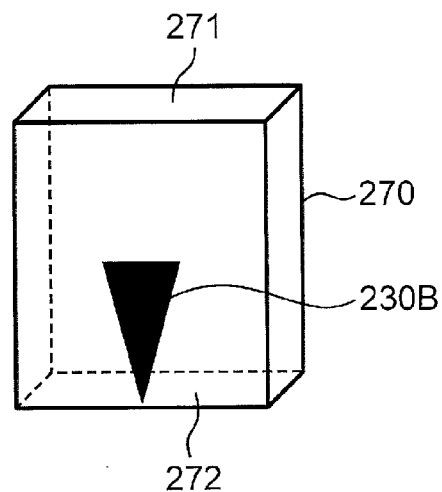
FIG. 8 is a schematic perspective view of another exemplary scattering substance (the fifth embodiment).

FIG. 8 is a schematic perspective view of the scattering substance 230B mounted on the substrate 270. The scattering substance 230B is described with reference to FIG. 8. It should be noted that the same reference numerals are assigned to the same components as those described in the context of the second embodiment. The description in the second embodiment is applicable to the components, to which the same reference numerals are assigned.

The scattering substance 230B shown in FIG. 8 is a pyramid pointed toward the second facing surface 272. The scattering substance 230B has a triangular cross section. A peak of an electric field amplitude caused by plasmon resonance is concentrated near the apex of the scattering substance 230B situated above or near the second facing surface 272. Consequently, there is enhanced detection sensitivity for reproduction signals.

Figure 9:
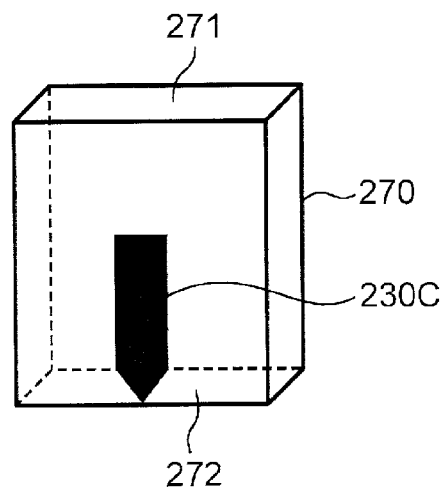
FIG. 9 is a schematic perspective view of yet another exemplary scattering substance (the fifth embodiment).

FIG. 9 is a schematic perspective view of the scattering substance 230C mounted on the substrate 270. The scattering substance 230C is described with reference to FIGS. 2 and 9. It should be noted that the same reference numerals are assigned to the same components as those described in the context of the second embodiment. The description in the second embodiment is applicable to the components, to which the same reference numerals are assigned.

The scattering substance 230C shown in FIG. 9 has a three-dimensional shape obtained by superimposing a cylindrical object situated within the substrate 270 with a pyramid pointed toward the second facing surface 272. The scattering substance 230C has a pentagonal cross section. Consequently, the scattering substance 230C has a wider reflection area than the scattering substance 230 described in the context of the second embodiment does, and concentrates a peak of electric field amplitude at the apex near the second facing surface 272.

In the aforementioned various embodiments, the scattering substances 230 to 230C have various cross section shapes such as a cylindrical shape, a diamond shape, a triangular shape or a pentagonal shape. Alternatively, the scattering substance may be designed to have another cross section shape. Apexes of the scattering substance may be designed to have a round shape if it is unnecessary for plasmon resonance to intensify a resultant electromagnetic field at the apex portions. Consequently, there is little unnecessary concentration of the electromagnetic field.

Sixth Embodiment

Configuration of Optical Pickup Device

Figure 10:
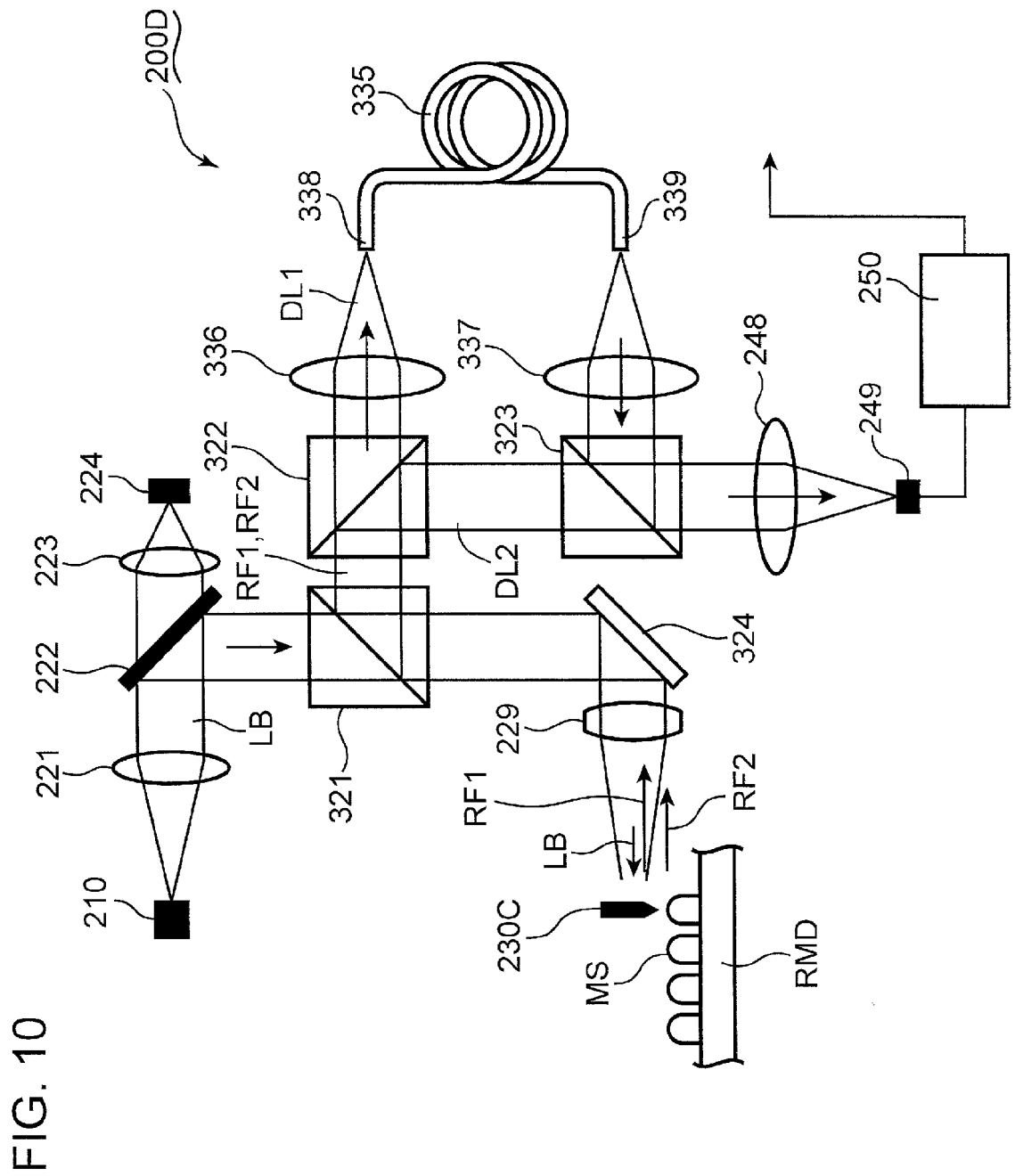
FIG. 10 is a schematic view of an optical pickup device exemplified as a detection device according to the sixth embodiment.

FIG. 10 is a schematic view of the optical pickup device 200D exemplified as the detection device. The optical pickup device 200D is designed on the basis of the principles of the detection device 100 described in the context of the first embodiment. The optical pickup device 200D is described with reference to FIGS. 1 and 10. It should be noted that the same reference numerals are assigned to the same components as those described in the context of the second and fifth embodiments. The descriptions in the second and fifth embodiments are applicable to the components, to which the same reference numerals are assigned.

In this embodiment, the optical pickup device 200D reproduces information from the recording medium RMD. A lot of micro structures MS are formed on a surface of the recording medium RMD. For example, the micro structures MS are granular phase change materials of 5 to 100 nanometers. The micro structures MS change phases between a crystalline state and a non-crystalline state (amorphous). Information (digital signals) is recorded on the recording medium RMD by using the phase change of the micro structures MS between the crystalline and non-crystalline states. In this embodiment, the micro structures MS correspond to the target object TO which is described with reference to FIG. 1.

Like the second embodiment, the optical pickup device 200D includes the laser beam source 210, the collimator lens 221, the mirror 222, the condensing lens 223, the light-receiving element 224, the objective lens 229, the detection lens 248, the photo-detector 249 and the signal processor 250. The optical pickup device 200D further includes the scattering substance 230C described in the context of the fifth embodiment.

The optical pickup device 200D further includes a first beam splitter 321, a second beam splitter 322, a third beam splitter 323, a reflecting mirror 324, an optical fiber 335, a condensing lens 336 and a collimator lens 337.

A part of the laser beam LB emitted from the laser beam source 210 is reflected by the mirror 222, and then travels toward the first beam splitter 321. The first beam splitter 321 allows passage of the laser beam LB reflected by the mirror 222. The laser beam LB thereafter travels toward the reflecting mirror 324.

The reflecting mirror 324 reflects the laser beam LB toward the objective lens 229. The objective lens 229 focuses the laser beam LB on the scattering substance 230C and the micro structures MS on the recording medium RMD. The scattering substance 230C reflects the laser beam LB to generate the reflected light RF1. The micro structures MS reflect the laser beam LB to generate the reflected light RF2. In this embodiment, the objective lens 229 is exemplified as the light guide portion. The reflected light RF1 from the scattering substance 230C is exemplified as the first reflected light. The reflected light RF2 from the micro structures MS are exemplified as the second reflected light.

Various designs about the scattering substance 230C and the micro structures MS such as a shape of the scattering substance 230C and a distance between the scattering substance 230C and the recording medium RMD are determined so that plasmon resonance is generated between the scattering substance 230C and the micro structures MS if the micro structures MS are crystals whereas there is no plasmon resonance generated between the scattering substance 230C and the micro structures MS if the micro structures MS are in the amorphous state. Like the second embodiment, the reflected light RF1 while plasmon resonance is generated between the scattering substance 230C and the micro structures MS is different in phase from the reflected light RF1 from the scattering substance 230C while no plasmon resonance is generated between the scattering substance 230C and the micro structures MS.

The reflected light RF1, which changes in phase in response to whether there is plasmon resonance generated between the scattering substance 230C and the micro structures MS, travels toward the objective lens 229. The reflected light RF2 from the micro structures MS also travels toward the objective lens 229, like the reflected light RF1. The objective lens 229 converts the reflected lights RF1, RF2 into collimated light. Subsequently, the reflected lights RF1, RF2 are reflected by the reflecting mirror 324, and then travel toward the first beam splitter 321.

The first beam splitter 321 reflects the reflected lights RF1, RF2 toward the second beam splitter 322. The second beam splitter 322 splits the reflected lights RF1, RF2 into first detection light DL1 and second detection light DL2.

The first detection light DL1 passes through the second beam splitter 322, and then travels toward the condensing lens 336. The optical fiber 335 includes an incident end 338, and an emission end 339 opposite to the incident end 338. The condensing lens 336 focuses the first detection light DL1 on the incident end 338. The first detection light DL1 entering the optical fiber 335 through the incident end 338 is emitted from the emission end 339.

The collimator lens 337 converts the first detection light DL1 emitted from the emission end 339 into collimated light. The first detection light DL1 passing through the collimator lens 337 travels toward the third beam splitter 323. The second detection light DL2 generated by the first beam splitter 321 directly travels from the first beam splitter 321 to the third beam splitter 323. Propagation of the first detection light DL1 in the third beam splitter 323 is delayed from the second detection light DL2 by a length of the optical fiber 335. In this embodiment, the optical fiber 335 is used for delaying the propagation of the first detection light DL1. Alternatively, another optical element configured to delay the propagation of the first detection light DL1 may be used instead of the optical fiber 335.

The third beam splitter 323 multiplexes the first and second detection lights DL1, DL2. The detection lens 248 focuses the multiplexed first and second detection lights DL1, DL2 on the photo-detector 249. The photo-detector 249 detects the state in phase of the reflected lights RF1, RF2 from the multiplexed first and second detection lights DL1, DL2.

The photo-detector 249 generates electric signals in response to intensity of the multiplexed first and second detection lights DL1, DL2. The electric signals are output from the photo-detector 249 to the signal processor 250. The signal processor 250 generates reproduction signals in response to the electric signals.

(Generation Principle of Reproduction Signals)

Figure 11:
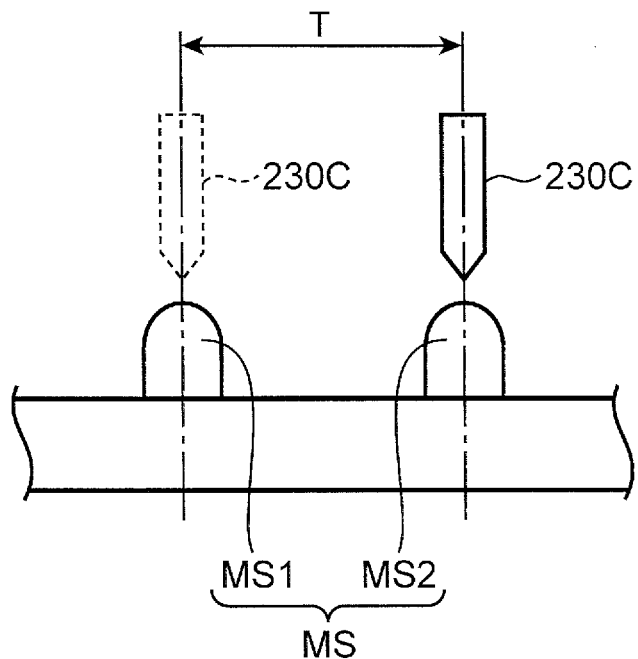
FIG. 11 is a schematic view of a scattering substance of the optical pickup device shown in FIG. 10.

FIG. 11 schematically represents the scattering substance 230C which moves above the micro structures MS. The generation principle of reproduction signals is described with reference to FIGS. 10 and 11.

FIG. 11 shows micro structures MS1, MS2 as the micro structures MS. The micro structure MS2 is situated adjacent to the micro structure MS1. The scattering substance 230C moves above the micro structure MS1, and then moves above the micro structure MS2.

FIG. 11 shows the time "T" from when the scattering substance 230C passes above the center of the micro structure MS1 to when the scattering substance 230C passes above the center of the micro structure MS2. The optical fiber 335 described with reference to FIG. 10 is designed to delay propagation of the first detection light DL1 from the second detection light DL2 by the time "T". Consequently, an interference state of the interfering light emitted from the third beam splitter 323 is changed by whether a state of the micro structure MS2 is the same as the micro structure MS1. The photo-detector 249 detects a change in the interference state as a light amount of the interfering light. Accordingly, the optical pickup device 200D may detect whether there is a change in the state of the micro structure MS to reproduce information.

Figure 12:
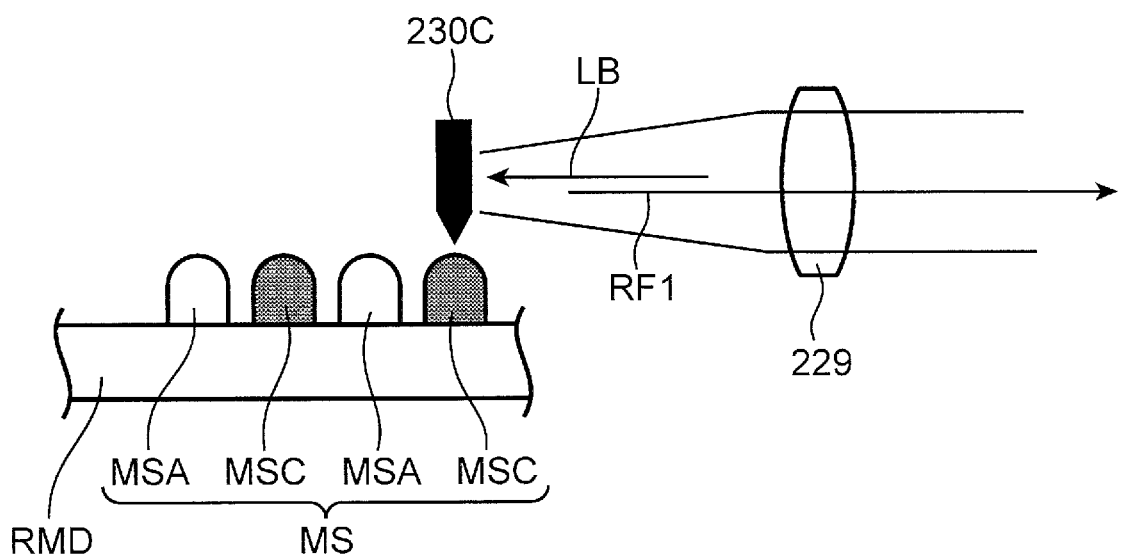
FIG. 12 is a schematic view of an exemplary recording pattern on a recording medium, which is used together with the optical pickup device shown in FIG. 10.

FIG. 12 is a schematic view of an exemplary recording pattern on the recording medium RMD. The recording pattern on the recording medium RMD is described with reference to FIG. 12.

In order to record information on the recording medium RMD, compositions or properties of the micro structures MS is associated with binary signals. In this embodiment, the micro structures MS are formed from phase change materials. Accordingly, the crystalline state and the non-crystalline state (amorphous) of the micro structures MS are associated with binary signals to record information on the recording medium RMD. FIG. 12 shows a micro structure MSC in the crystalline state and a micro structure MSA in the non-crystalline state (amorphous) as the micro structures MS.

As described in the context of the second embodiment, the generation of plasmon resonance is dependent on a relationship between a wavelength of the laser beam LB irradiating the scattering substance 230C and a length of the scattering substance 230C. As shown in FIG. 12, a condition (condition about the length of the scattering substance 230C) for generating plasmon resonance between the scattering substance 230C and the micro structure MSC is different from a condition (condition about the length of the scattering substance 230C) for generating plasmon resonance between the scattering substance 230C and the micro structure MSA. Accordingly, a phase of the reflected light RF1 from the scattering substance 230C is changed by the state of the micro structure MS to which the scattering substance 230C gets closer.

Figure 13:
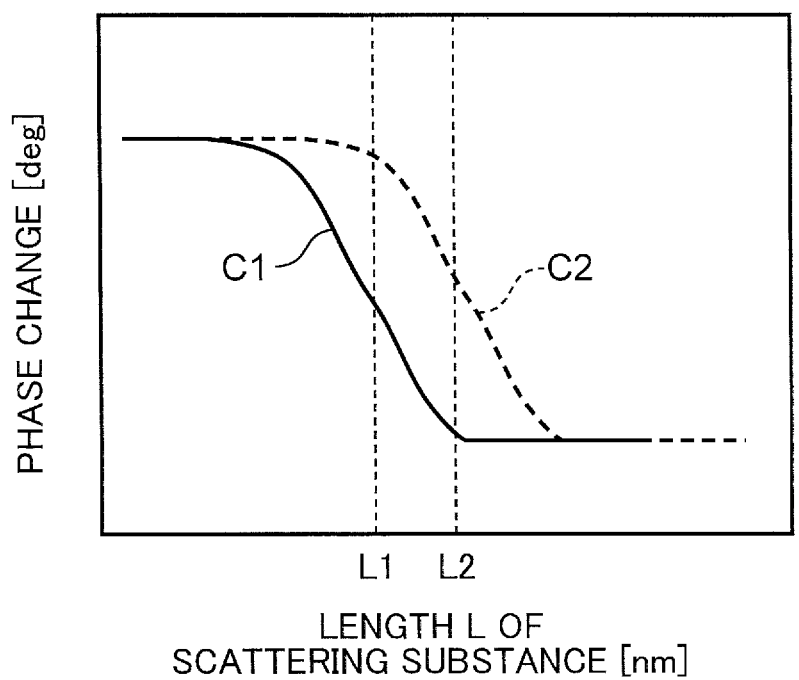
FIG. 13 is a schematic graph showing a relationship between a phase of the reflected light from the scattering substance and a length of the scattering substance.

FIG. 13 is a schematic graph showing a relationship between a phase of the reflected light RF1 from the scattering substance 230C and a length of the scattering substance 230C. The relationship between the phase of the reflected light RF1 from the scattering substance 230C and the length of the scattering substance 230C is described with reference to FIGS. 12 and 13.

In FIG. 13, a length (antenna length) when the scattering substance 230C getting closer to the micro structure MSC (crystalline state) generates plasmon resonance is represented with the symbol "L1". The length (antenna length) when the scattering substance 230C getting closer to the micro structure MSA (non-crystalline state) generates plasmon resonance is represented with the symbol "L2".

In FIG. 13, the relationship between a length of the scattering substance 230C getting closer to the micro structure MSC and a phase of the reflected light RF1 from the scattering substance 230C is shown with the curve C1. The relationship between a length of the scattering substance 230C getting closer to the micro structure MSA and a phase of the reflected light RF1 from the scattering substance 230C is shown with the curve C2. The curve C2 is shifted from the curve C1 in the length of the scattering substance 230C.

When the length of the scattering substance 230C is "L1", the reflected light RF1 generated from the scattering substance 230C getting closer to the micro structure MSC is different in phase from the reflected light RF1 generated from the scattering substance 230C getting closer to the micro structure MSA. A state of the micro structures MS may be identified by detection of the phase difference of the reflected light RF1. Accordingly, the information recorded on the recording medium RMD may be accurately reproduced.

In this embodiment, the micro structures MS formed on the recording medium RMD are used as the target object. Since the micro structures MS include phase change materials, the micro structures MS become the crystalline or non-crystalline state. In this embodiment, the micro structures MS are exemplified as the structures.

Intensity of the plasmon resonance generated between the micro structure MS and the scattering substance 230C is changed by a state (crystalline state or non-crystalline state) of the micro structures MS. The optical pickup device 200D according to this embodiment detects the state in phase of the reflected light RF1 from the scattering substance 230C to identify whether the micro structures MS are in the crystalline or non-crystalline state. The crystalline state of the micro structure MS corresponds to one of the recorded and unrecorded states whereas the non-crystalline state corresponds to the other of the recorded and unrecorded states. Accordingly, the optical pickup device 200D may detect whether the micro structures MS are in the crystalline or non-crystalline state to identify whether the micro structures MS are in the recorded or unrecorded state.

The optical pickup device 200D according to this embodiment may detect a state of the micro structures MS used as the target object with high sensitivity and little noise. In this embodiment, the optical pickup device 200D may be designed so that plasmon resonance is generated when the scattering substance 230C gets closer to the micro structures MS in the crystalline state. In this case, the optical pickup device 200D may be designed so that no plasmon resonance is generated when the scattering substance 230C gets closer to the micro structures MS in the non-crystalline state. In other words, the optical pickup device 200D may be designed so that intensity of the plasmon resonance between the scattering substance 230C and the micro structure MSC in the non-crystalline state becomes "0".

Alternatively, the optical pickup device 200D may be designed so that plasmon resonance is generated when the scattering substance 230C gets closer to the micro structures MS in the non-crystalline state. In this case, the optical pickup device 200D may be designed so that no plasmon resonance is generated when the scattering substance 230C gets closer to the micro structures MS in the crystalline state. In other words, the optical pickup device 200D may be designed so that intensity of the plasma resonance between the scattering substance 230C and the micro structure MSC in the crystalline state becomes "0".

The light guide portion (objective lens 229) (c.f. FIG. 10) of the optical pickup device 200D may emit the laser beam LB to irradiate not only the micro structures MS used as the target object but also the scattering substance 230C. In this case, the detector (detection lens 248 and photo-detector 249) (c.f. FIG. 10) may detect not only the state in phase of the reflected light RF2 from the micro structures MS but also the state in phase of the reflected light RF1 from the scattering substance 230C. Due to interaction between the reflected lights RF1, RF2, the optical pickup device 200D may detect the state in phase of the reflected light RF1 with high sensitivity. In other words, since the phase of the reflected light RF2 from the micro structures MS is detected in addition to the phase of the reflected light RF1 from the scattering substance 230C, the optical pickup device 200D may detect the state in phase of the reflected light RF1 with high sensitivity.

In this embodiment, the optical fiber 335 (c.f. FIG. 10) is used for delaying the first detection light DL1. A resultant delay time of the first detection light DL1 from the optical fiber 335 is set to be equal to a time interval which is required for the scattering substance 230C to move above between the centers of the micro structures MS. Alternatively, if a delay time of the first detection light DL1 caused by the optical fiber 335 and an arrangement interval of the micro structures MS are known, arithmetic processes may be performed for signals indicating a light amount change instead of the optical configuration for causing the delay. The state of the micro structures MS may be identified on the basis of the arithmetic processes.

In this embodiment, a length of the scattering substance 230C is designed so that plasmon resonance is generated in cooperation with the micro structures MS in the crystalline or non-crystalline state. Alternatively, the length of the scattering substance 230C may be set to an intermediate value of the size values "L1", "L2" shown in FIG. 13. Even with such a design, since the phase of the detected light is changed by the state of the micro structures MS, information may be appropriately reproduced from the recording medium RMD.

In this embodiment, the micro structures MS include phase change materials. Information is reproduced on the basis of the change in a phase state of the micro structures MS. Alternatively, a difference in materials between the micro structures MS (e.g. dielectric material and metal) or a difference in electrical resistance, refractive index or shape between the micro structures MS may be used as a factor to change the resonance state.

Seventh Embodiment

Configuration of Optical Pickup Device

Figure 14:
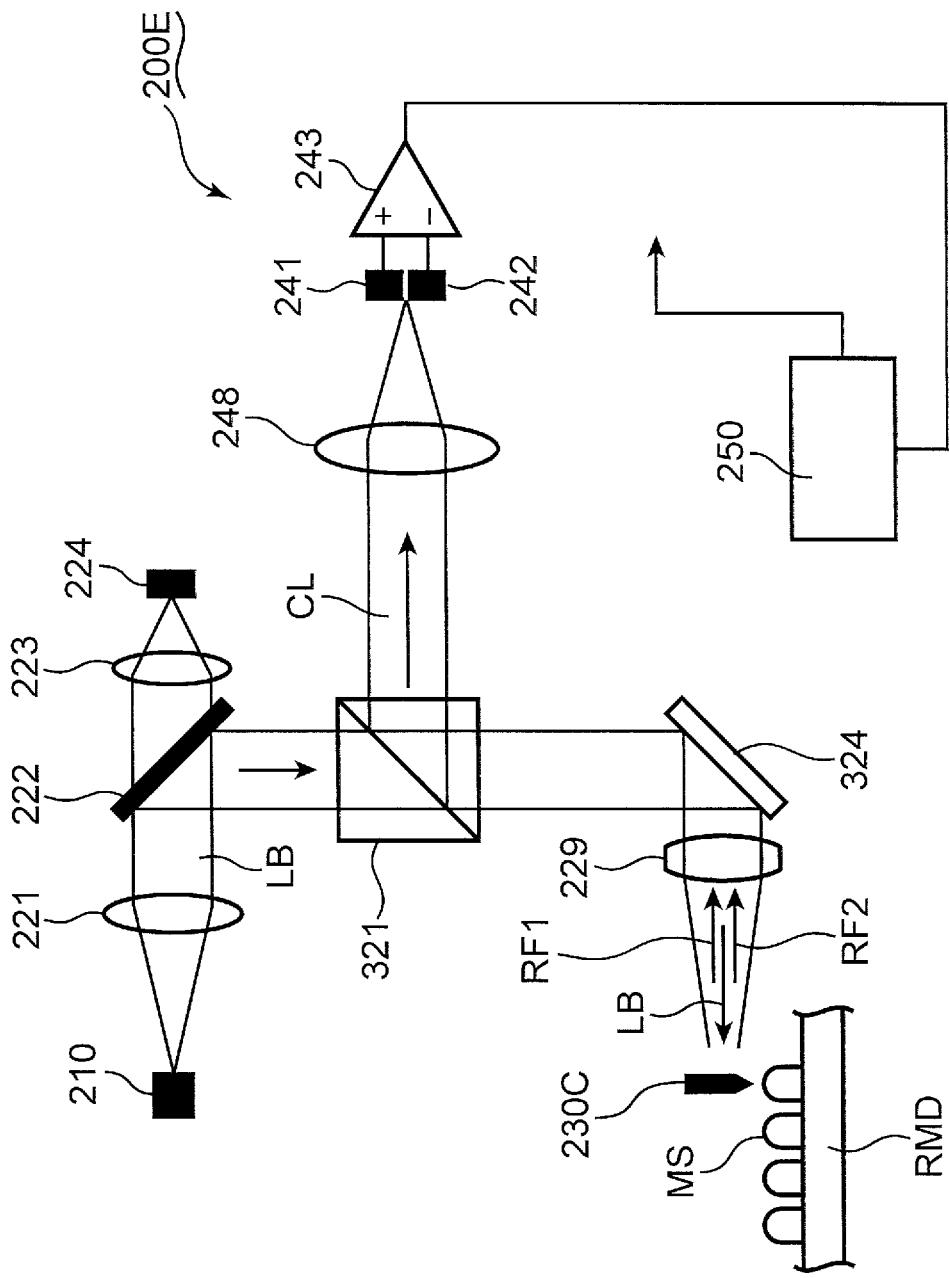
FIG. 14 is a schematic view of an optical pickup device exemplified as a detection device according to the seventh embodiment.

FIG. 14 is a schematic view of the optical pickup device 200E exemplified as the detection device. The optical pickup device 200E is designed on the basis of the principles of the detection device 100 described in the context of the first embodiment. The optical pickup device 200E is described with reference to FIG. 14. It should be noted that the same reference numerals are assigned to the same components as those described in the context of the second and sixth embodiments. The descriptions in the second and sixth embodiments are applicable to the components, to which the same reference numerals are assigned.

Like the second embodiment, the optical pickup device 200E includes the laser beam source 210, the collimator lens 221, the mirror 222, the condensing lens 223, the light-receiving element 224, the objective lens 229, the detection lens 248 and the signal processor 250. Like the sixth embodiment, the optical pickup device 200E further includes the scattering substance 230C, the first beam splitter 321 and the reflecting mirror 324. The optical pickup device 200E further includes a first photo-detector 241, a second photo-detector 242 and an arithmetic circuit 243.

Like the sixth embodiment, the optical pickup device 200E uses the micro structures MS to reproduce information from the recording medium RMD on which digital information is recorded. The scattering substance 230C is situated near the micro structures MS. The plasmon resonance between the micro structures MS and the scattering substance 230C is used for the reproduction of the information. It should be noted that the micro structures MS may be granular phase change materials of 5 to 100 nanometers. Digital signal information is recorded on the recording medium RMD by using a difference in a state (crystalline state or non-crystalline state (amorphous)) of the micro structures MS.

Like the sixth embodiment, the laser beam source 210 emits the laser beam LB. The mirror 222 partially reflects the laser beam LB toward the first beam splitter 321. The first beam splitter 321 allows passage of the laser beam LB reflected by the mirror 222. Consequently, the laser beam LB reaches the reflecting mirror 324. The reflecting mirror 324 reflects the laser beam LB toward the objective lens 229.

Like the sixth embodiment, the objective lens 229 emits the laser beam LB toward the scattering substance 230C and the micro structure MS. The scattering substance 230C reflects the laser beam LB to generate the reflected light RF1. The micro structure MS reflects the laser beam LB to generate the reflected light RF2. A phase of the reflected light RF1 is changed by intensity of the plasmon resonance. The scattering substance 230C and the micro structures MS are designed to generate plasmon resonance between the scattering substance 230C and the micro structures MS in response to the irradiation of the laser beam LB when the micro structure MS is in the crystalline state. The scattering substance 230C and the micro structure MS are designed so that no plasmon resonance is generated between the scattering substance 230C and the micro structure MS when the micro structure MS is in the non-crystalline state (amorphous). Otherwise, the scattering substance 230C and the micro structure MS may be designed so that there is weaker plasmon resonance between the scattering substance 230C and the micro structure MS when the micro structure MS is in the non-crystalline state (amorphous). In this embodiment, the reflected light RF1 is exemplified as the first reflected light. The reflected light RF2 is exemplified as the second reflected light.

The reflected lights RF1, RF2 are converted into collimated light by the objective lens 229. The reflected lights RF1, RF2 are then reflected toward the first beam splitter 321 by the reflecting mirror 324. The first beam splitter 321 reflects the reflected lights RF1, RF2 toward the detection lens 248. The reflected lights RF1, RF2 are multiplexed in a path from the scattering substance 230C and the micro structure MS to the detection lens 248, and become synthetic waves CL. In this embodiment, the reflecting mirror 324 and the first beam splitter 321 situated on a propagation path of the synthetic waves CL are exemplified as the synthesizer.

The detection lens 248 focuses the synthetic waves CL toward a bisection detector formed from the first and second photo-detectors 241, 242. An inclination of the optical axis of the synthetic waves CL is changed by intensity of the plasmon resonance between the scattering substance 230C and the micro structures MS. The first and second photo-detectors 241, 242 and the arithmetic circuit 243 detect the inclination of the optical axis of the synthetic waves CL. A phase of the reflected light RF1 is detected with reference to the detected inclination. In this embodiment, the first and second photo-detectors 241, 242 and the arithmetic circuit 243 are exemplified as the inclination detector.

According to the principles of this embodiment, a state of the target object (micro structures MS) and information recorded on the target object are detected with high sensitivity and little noise since the optical pickup device 200E detects the inclination of the optical axis of the synthetic waves CL which indicates the state in phase of the reflected light RF1.

Figure 15A:
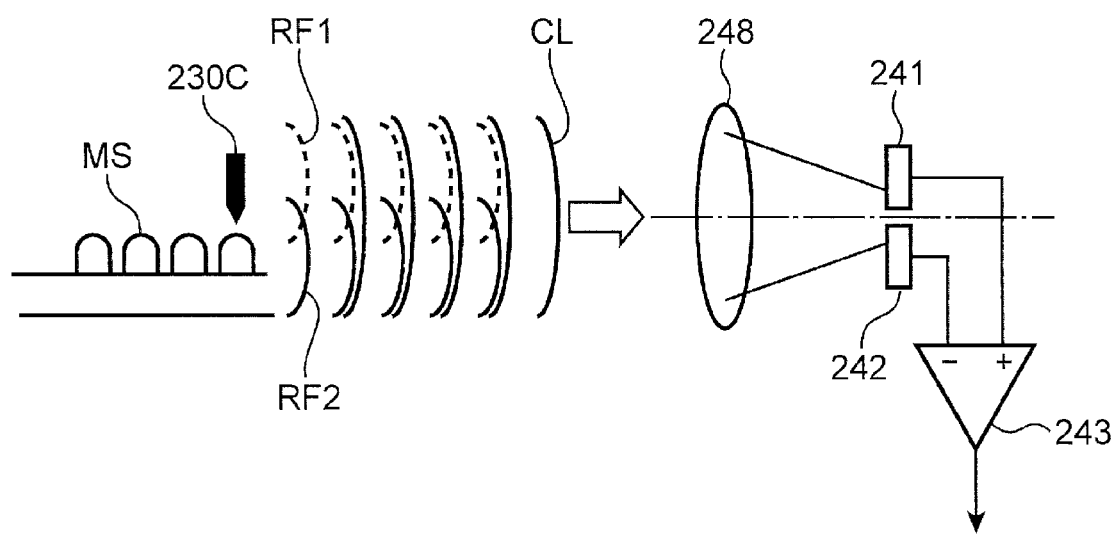
FIG. 15A is a schematic view of detection techniques of an inclination of an optical axis of synthetic waves generated in the optical pickup device shown in FIG. 14.
Figure 15B:
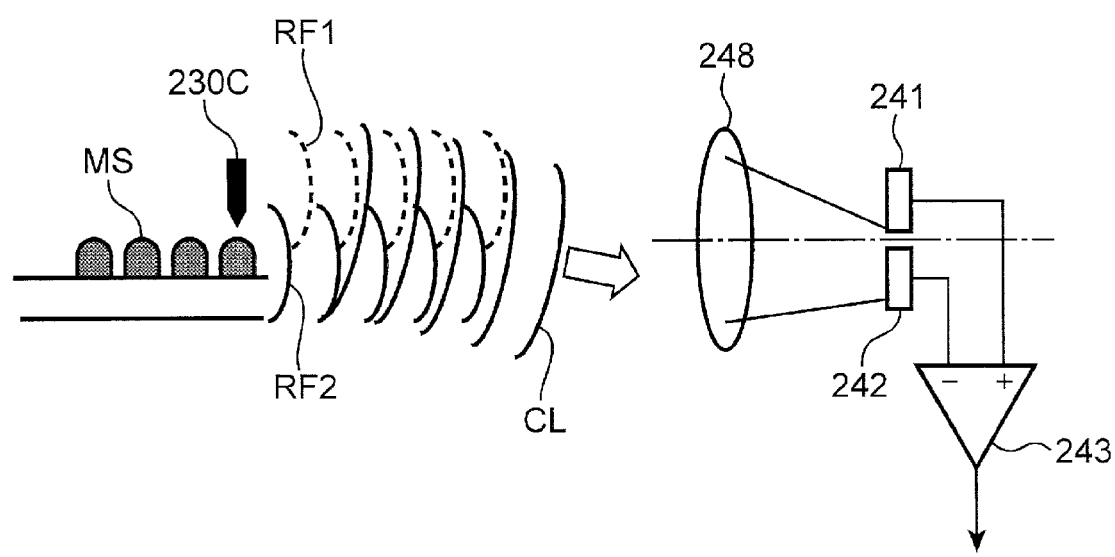
FIG. 15B is a schematic view of the detection techniques of the inclination of the optical axis of the synthetic waves generated in the optical pickup device shown in FIG. 14.

FIGS. 15A and 15B are schematic views showing a relationship between the inclination of the optical axis of the synthetic waves CL and the detection of the inclination of the optical axis of the synthetic waves CL by means of the first and second photo-detectors 241, 242. The inclination of the optical axis of the synthetic waves CL and the detection of the inclination of the optical axis of the synthetic waves CL are described with reference to FIGS. 14 to 15B.

The micro structures MS shown in FIG. 15A are in the non-crystalline state (amorphous). In this case, no plasma resonance is generated between the scattering substance 230C and the micro structures MS. Accordingly, the phase of the reflected light RF1 from the scattering substance 230C coincides with the phase of the reflected light RF2 from the micro structures MS. Meanwhile, the synthetic waves CL, which reach the first and second photo-detectors 241, 242 through the first beam splitter 321 and the detection lens 248, are emitted substantially evenly to the first and second photo-detectors 241, 242.

The micro structures MS shown in FIG. 15B are in the crystalline state. In this case, plasmon resonance is generated between the scattering substance 230C and the micro structures MS. As a result of the plasmon resonance, there may be a difference in phase between the reflected light RF1 from the scattering substance 230C and the reflected light RF2 from the micro structures MS. The phase of the reflected light RF2 shown in FIG. 15B is delayed from the reflected light RF1. The phase delay of the reflected light RF2 from the reflected light RF1 causes a change in the inclination of the optical axis of the synthetic waves CL. Accordingly, the second photo-detector 242 detects a light amount larger than the first photo-detector 241 does. It should be noted that the plasmon resonance may result in a phase delay of the reflected light RF1 from the reflected light RF2. In this case, there is also a change in the inclination of the optical axis of the synthetic waves CL. Consequently, the first photo-detector 241 may detect a light amount greater than the second photo-detector 242 may do.

As described above, the synthetic waves CL are reflected toward the detection lens 248 by the first beam splitter 321. The detection lens 248 makes the synthetic waves CL converge on the bisection detector formed from the first and second photo-detectors 241, 242. Consequently, a light focusing spot is formed on the bisection detector.

Figure 16A:
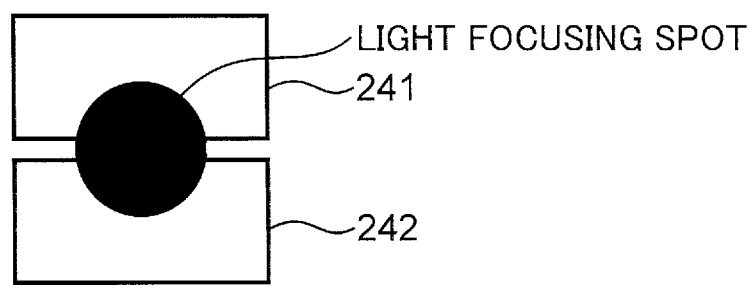
FIG. 16A is a schematic view of a light focusing spot of the synthetic waves shown in FIG. 15A.
Figure 16B:
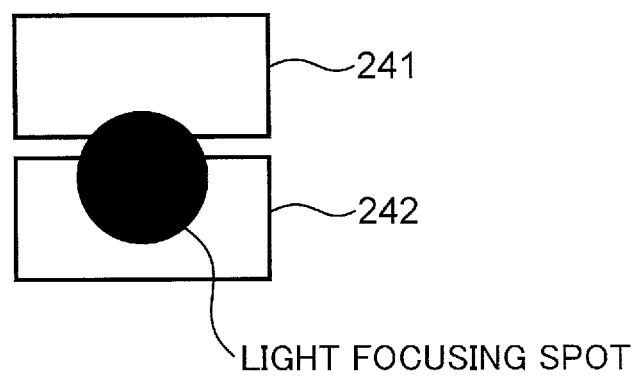
FIG. 16B is a schematic view of a light focusing spot of the synthetic waves shown in FIG. 15B.

FIGS. 16A and 16B are schematic views of the light focusing spot on the bisection detector. The detection principle of the inclination of the optical axis of the synthetic waves CL is described with reference to FIGS. 14 to 16B.

FIG. 16A corresponds to FIG. 15A. In other words, FIG. 16A shows a light focusing spot without plasmon resonance generated between the scattering substance 230C and the micro structures MS. The light focusing spot shown in FIG. 16A is formed substantially at the center of a surface of the bisection detector. The first and second photo-detectors 241, 242 output electric signals to the arithmetic circuit 243 in response to a received light amount. The arithmetic circuit 243 performs a difference operation to the electric signals from the first and second photo-detectors 241, 242. Accordingly, as shown in FIG. 16A, the differential output from the arithmetic circuit 243 becomes substantially "0" when the light focusing spot is formed at substantially the center of the surface of the bisection detector.

FIG. 16B corresponds to FIG. 15B. In other words, FIG. 16B shows a light focusing spot when plasmon resonance is generated between the scattering substance 230C and the micro structures MS. The light focusing spot shown in FIG. 16B is shifted from the center of the bisection detector, so that the second photo-detector 242 receives more synthetic waves CL. Consequently, there may be a change in the differential output generated by the difference operation performed to the electric signals from the first and second photo-detectors 241, 242.

As described above, the electric signals from the first and second photo-detector 241, 242 are changed by the change in the inclination of the optical axis of the synthetic waves. The arithmetic circuit 243 may perform a difference operation to these electric signals to detect the inclination of the optical axis of the synthetic waves CL. Signals indicating the inclination of the optical axis of the synthetic waves CL are output from the arithmetic circuit 243 to the signal processor 250. The signal processor 250 may generate reproduction signals in response to the signals from the arithmetic circuit 243.

The optical pickup device 200E according to this embodiment uses the reflected light RF1 from the scattering substance 230C and the reflected light RF2 from the micro structures MS to detect the change in the inclination of the synthetic waves CL, and then generates reproduction signals. Alternatively, the optical pickup device may detect a change in the optical axis of transmitted lights from the scattering substance and/or the micro structures to generate reproduction signals.

Eighth Embodiment

Configuration of Optical Pickup Device

Figure 17:
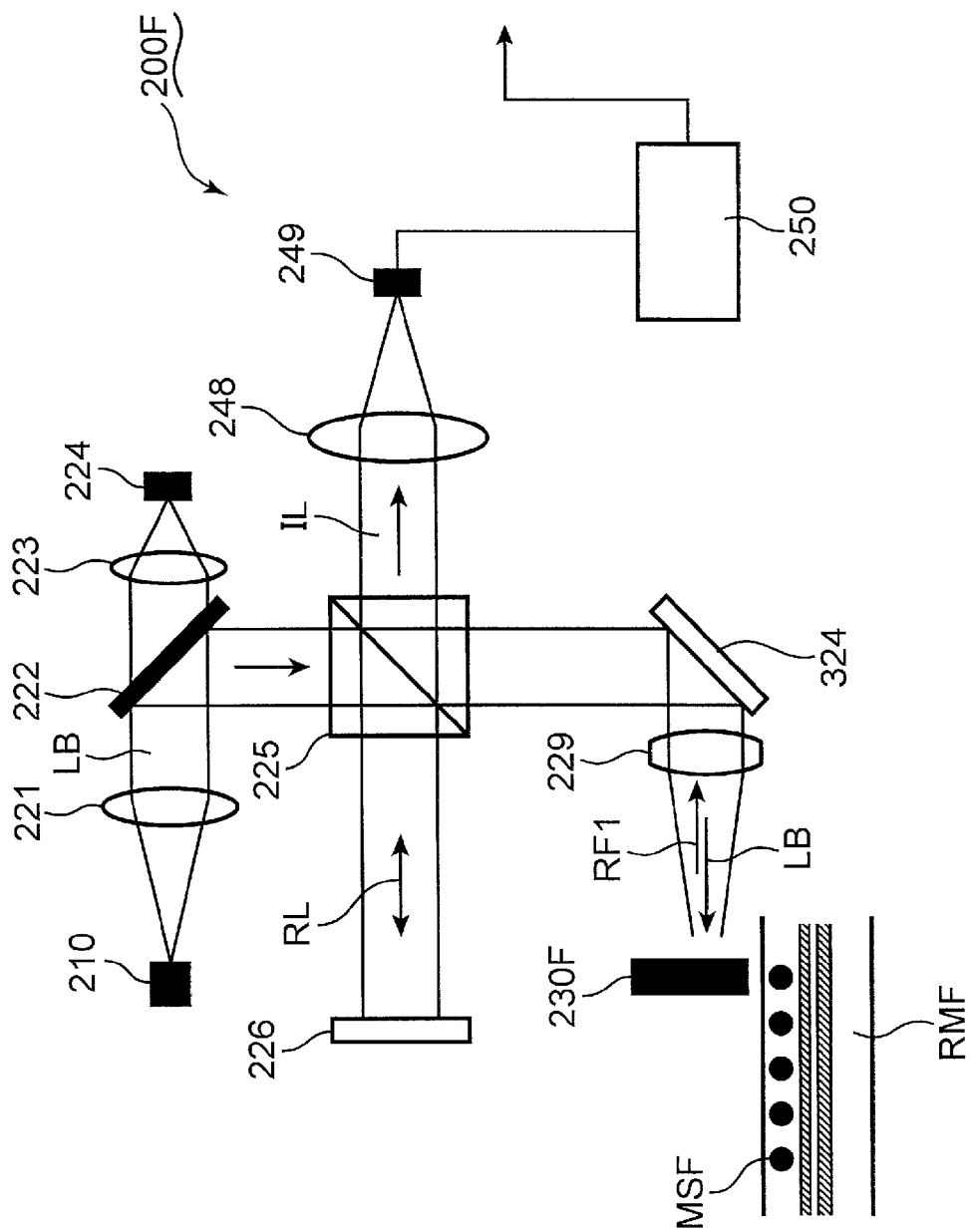
FIG. 17 is a schematic view of an optical pickup device exemplified as a detection device according to the eighth embodiment.

FIG. 17 is a schematic view of the optical pickup device 200F exemplified as the detection device. The optical pickup device 200F is designed on the basis of the principles of the detection device 100 described in the context of the first embodiment. The optical pickup device 200F is described with reference to FIG. 17. It should be noted that the same reference numerals are assigned to the same components as those described in the context of the second and seventh embodiments. The descriptions in the second and seventh embodiments are applicable to the components, to which the same reference numerals are assigned.

Like the second embodiment, the optical pickup device 200F includes the laser beam source 210, the collimator lens 221, the mirror 222, the condensing lens 223, the light-receiving element 224, the beam splitter 225, the mirror 226, the detection lens 248, the photo-detector 249 and the signal processor 250. Like the seventh embodiment, the optical pickup device 200F further includes the reflecting mirror 324 and the objective lens 229. The optical pickup device 200F further includes a scattering substance 230F.

The laser beam source 210 emits the laser beam LB toward the collimator lens 221. The collimator lens 221 converts the laser beam LB into collimated light. Subsequently, the mirror 222 reflects a part of the laser beam LB toward the beam splitter 225.

The beam splitter 225 splits a part of the laser beam LB reflected by the mirror 222 as reference light RL. The beam splitter 225 allows passage of the remaining part of the laser beam LB. The laser beam LB passing through the beam splitter 225 is reflected toward the objective lens 229 by the reflecting mirror 324. The objective lens 229 focuses the laser beam LB on the scattering substance 230F. Consequently, localized plasmon happens to the scattering substance 230F. Accordingly, the optical electric field is intensified near the scattering substance 230F.

The scattering substance 230F reflects the laser beam LB to generate the reflected light RF1. The reflected light RF1 is converted into collimated light by the objective lens 229. Subsequently, the reflecting mirror 324 reflects the reflected light RF1 toward the beam splitter 225.

The reference light RL generated by the beam splitter 225 is reflected toward the beam splitter 225 by the mirror 226. The beam splitter 225 allows passage of the reference light RL reflected from the mirror 226. On the other hand, the reflected light RF1 after reflection from the reflecting mirror 324 is further reflected toward the detection lens 248 by the beam splitter 225. Since both of the reference light RL and the reflected light RF1 travel toward the detection lens 248, they are multiplexed between the beam splitter 225 and the detection lens 248 to become interfering light IL. The interfering light IL is focused on the photo-detector 249 by the detection lens 248.

In this embodiment, the optical pickup device 200F reproduces information from the recording medium RMF. The phase of the reflected light RF1 is changed by the intensity of the plasmon resonance, which is generated by interaction between the recording mark recorded on a surface of the recording medium RMF and the laser beam LB. Accordingly, intensity of the interfering light IL is changed considerably by the intensity of the plasmon resonance. The optical pickup device 200F detects the change in the intensity of the interfering light IL to generate information from the recording medium RMF.

Electric signals output from the photo-detector 249 are changed by the intensity of the interfering light IL. The signal processor 250 generates and outputs reproduction signals in response to the electric signals from the photo-detector 249. Accordingly, the optical pickup device 200F may accurately output the information recorded on the recording medium RMF as digital signals.

Figure 18A:
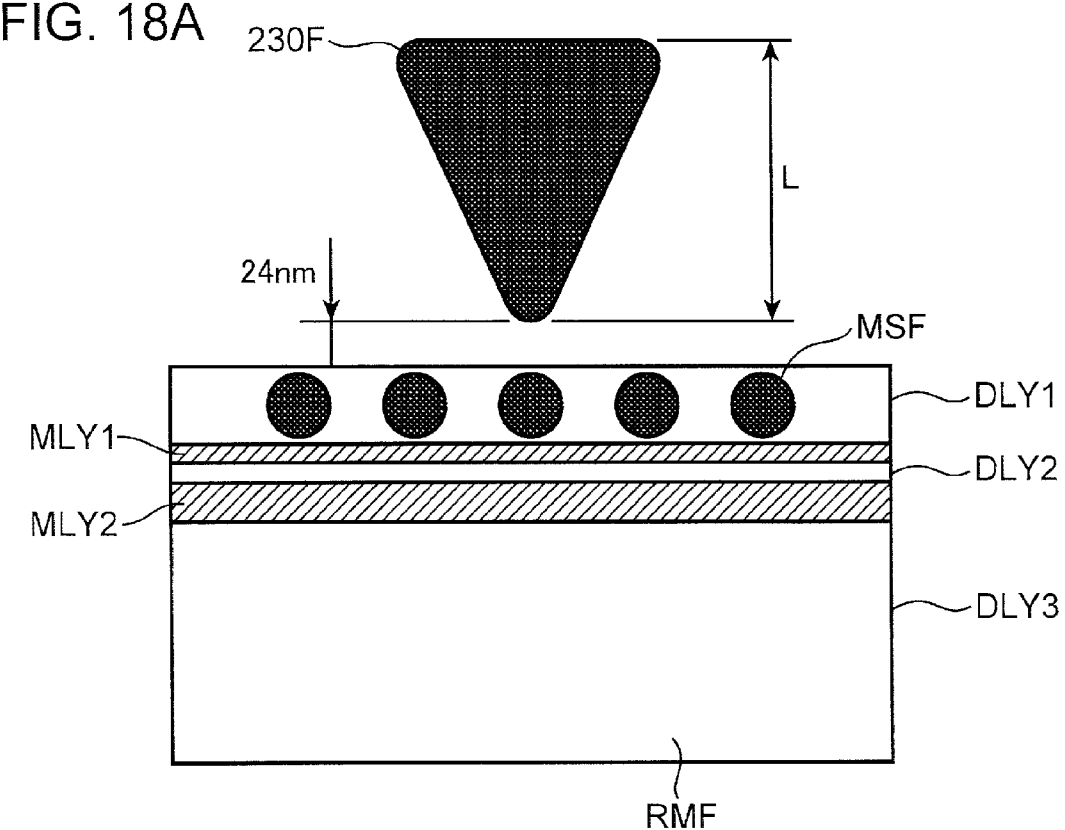
FIG. 18A is a schematic front view of a scattering substance and a recording medium.
Figure 18B:
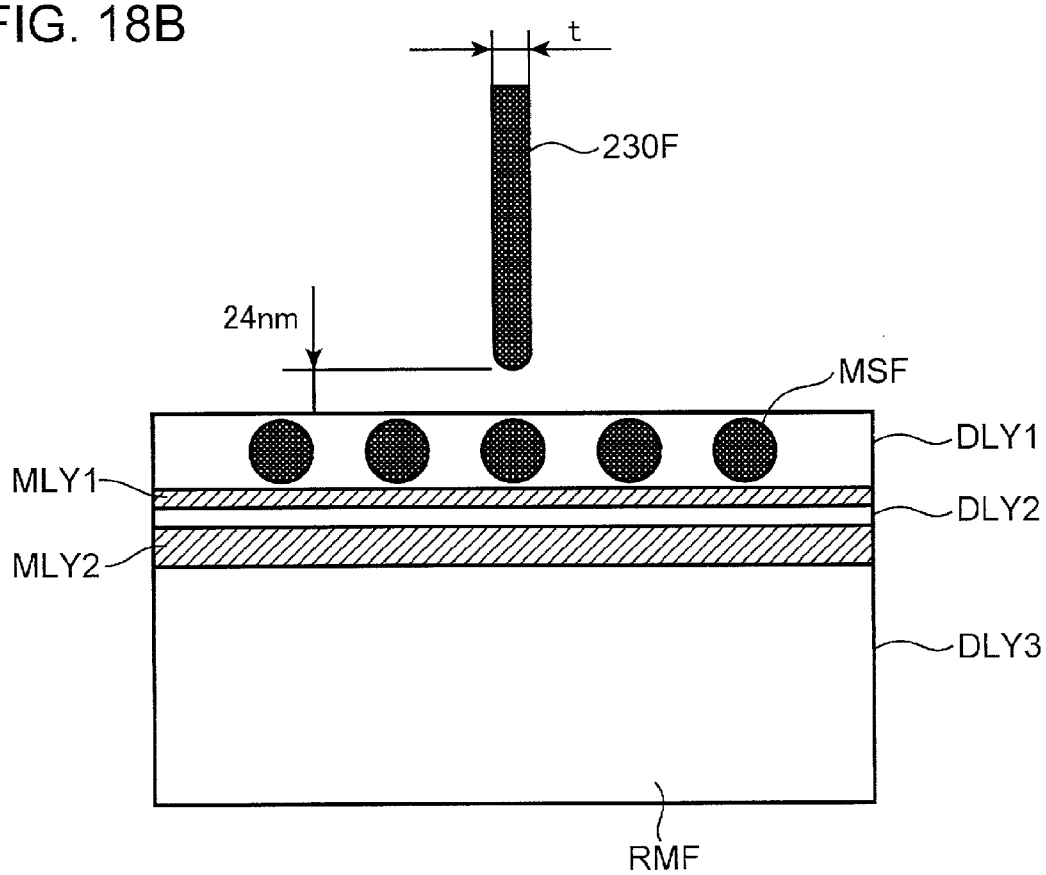
FIG. 18B is a schematic side view of a scattering substance and a recording medium.

FIG. 18A is a schematic front view of the scattering substance 230F and the recording medium RMF. FIG. 18B is a schematic side view of the scattering substance 230F and the recording medium RMF. The scattering substance 230F and the recording medium RMF are described with reference to FIGS. 17 to 18B.

The scattering substance 230F used in the optical pickup device 200F according to this embodiment is substantially triangular. The length "L" (size in a direction orthogonal to the recording medium RMF) of the scattering substance 230F is 120 nm, and the thickness "t" of the scattering substance 230F is 24 nm. The scattering substance 230F is formed from silver. The apex angle of the scattering substance 230F is designed to be "45°". It should be noted that the respective apexes of the scattering substance 230F are curved at a curvature of 12 nm.

The recording medium RMF has a disk shape. The recording medium RMF includes a first metal layer MLY1, and a second metal layer MLY2 formed below the first metal layer MLY1. The first metal layer MLY1 is a silver thin film which is 8 nm in thickness. The second metal layer MLY2 is a silver thin film which is 20 nm in thickness.

The recording medium RMF includes a first dielectric layer DLY1 formed on the first metal layer MLY1, a second dielectric layer DLY2, which is interposed between the first and second metal layers MLY1, MLY2, and a third dielectric layer DLY3 formed below the second metal layer MLY2. The first dielectric layer DLY1 is a $SO_2$ thin film which is 32 nm in thickness. The second dielectric layer DLY2 is a $SiO_2$ thin film which is 4 nm in thickness. The third dielectric layer DLY3 is a $SiO_2$ thin film which is a few millimeters in thickness. The third dielectric layer DLY3 is used as a substrate.

The micro structures MSF are situated inside the first dielectric layer DLY1. The micro structures MSF are silver fine particles which is 24 nm in diameter. Digital signals are recorded on the basis of presence or absence of the micro structures MSF.

A position of the scattering substance 230F is controlled so that the scattering substance 230F is distant from the first dielectric layer DLY1 by 24 nm.

The laser beam LB emitted from the laser beam source 210 described with reference to FIG. 17 is 780 nm in wavelength. The branch ratio of the beam splitter 225 is set to 1:1. The numerical aperture of the objective lens 229 is set to "0.7". Without the micro structures MSF in a detection target area on the recording medium RMF, the mirror 226 is positioned so that the intensity of the interfering light IL, which is generated from the reference light RL reflected from the mirror 226 and the reflected light RF1 from the scattering substance 230F, is minimized. Consequently, the phase of the reference light RL is appropriately adjusted.

As described with reference to FIG. 17, the laser beam LB is emitted to the scattering substance 230F through the objective lens 229. The scattering substance 230F reflects the laser beam LB to generate the reflected light RF1. The present inventors used the FDTD method to simulate power reflectance of the resultant reflected light RF1 from reflection at the scattering substance 230F. As a result of performing calculations during the simulation, without the micro structures MSF in the detection target area on the recording medium RMF, the power reflectance was 2.48% for the laser beam LB passing through the objective lens 229. With the micro structures MSF in the detection target area on the recording medium RMF, the power reflectance was 3.38%.

The present inventors computed the phase of the interfering light IL, which is generated from the reference light RL reflected from the mirror 226 and the reflected light RF1 from the scattering substance 230F, on the basis of the simulation using the FDTD method. A phase change amount of the interfering light IL between a condition, in which there were no micro structures MSF in the detection target area on the recording medium RMF, and a condition where there were the micro structures MSF in the detection target area on the recording medium RMF was 8.62 degrees.

A light amount I of the reflected light RF1 in the photo-detector 249 described with reference to FIG. 17 is expressed with the following formula.

$$I = 0.5 \times (I_i + I_r) + 2 \times \sqrt{I_i I_r} \times \sin \phi \quad \text{[Formula 2]}$$

"$I_i$" is an incident light amount of the laser beam LB which enters the objective lens 229. "$I_r$" is a light amount of the reflected light RF1 emitted from the objective lens 229. "$\phi$" is a phase of the reflected light RF1.

When there are the micro structures MSF, the optical pickup device 200F is adjusted in advance so that the phase of the interfering light IL satisfies a relationship of "$\phi=0$". Accordingly, when there are the micro structures MSF, a relationship of "I=51.69%" is obtained. Without the micro structures MSF, as described above, a relationship of "$\phi=8.62°$" is obtained. Accordingly, without the micro structures MSF, a relationship of "I=53.6%" is obtained. Consequently, the power reflectance changes by "1.91%" in response to whether there are the micro structures MSF.

The power reflectance was compared between an optical system, in which the mirror 226 had been removed from the optical pickup device 200F described with reference to FIG. 17, and the optical pickup device 200F. According to the optical system under the removal of the mirror 226, a power reflectance variation, which depends only on reflectance change, is obtained. In this case, "0.45%" of the power reflectance variation is easily calculated out in light of "1:1" of the branch ratio of the beam splitter 225.

Signal detection sensitivity of the signal detection techniques utilizing the phase change of the reflected light RF1 becomes approximately 4.2 times as high as signal detection sensitivity of the signal detection techniques which do not utilize the phase change of the reflected light RF1. Accordingly, the detection sensitivity may be considerably enhanced by use of the phase change of the reflected light RF1.

Ninth Embodiment

Configuration of Optical Pickup Device

Figure 19:
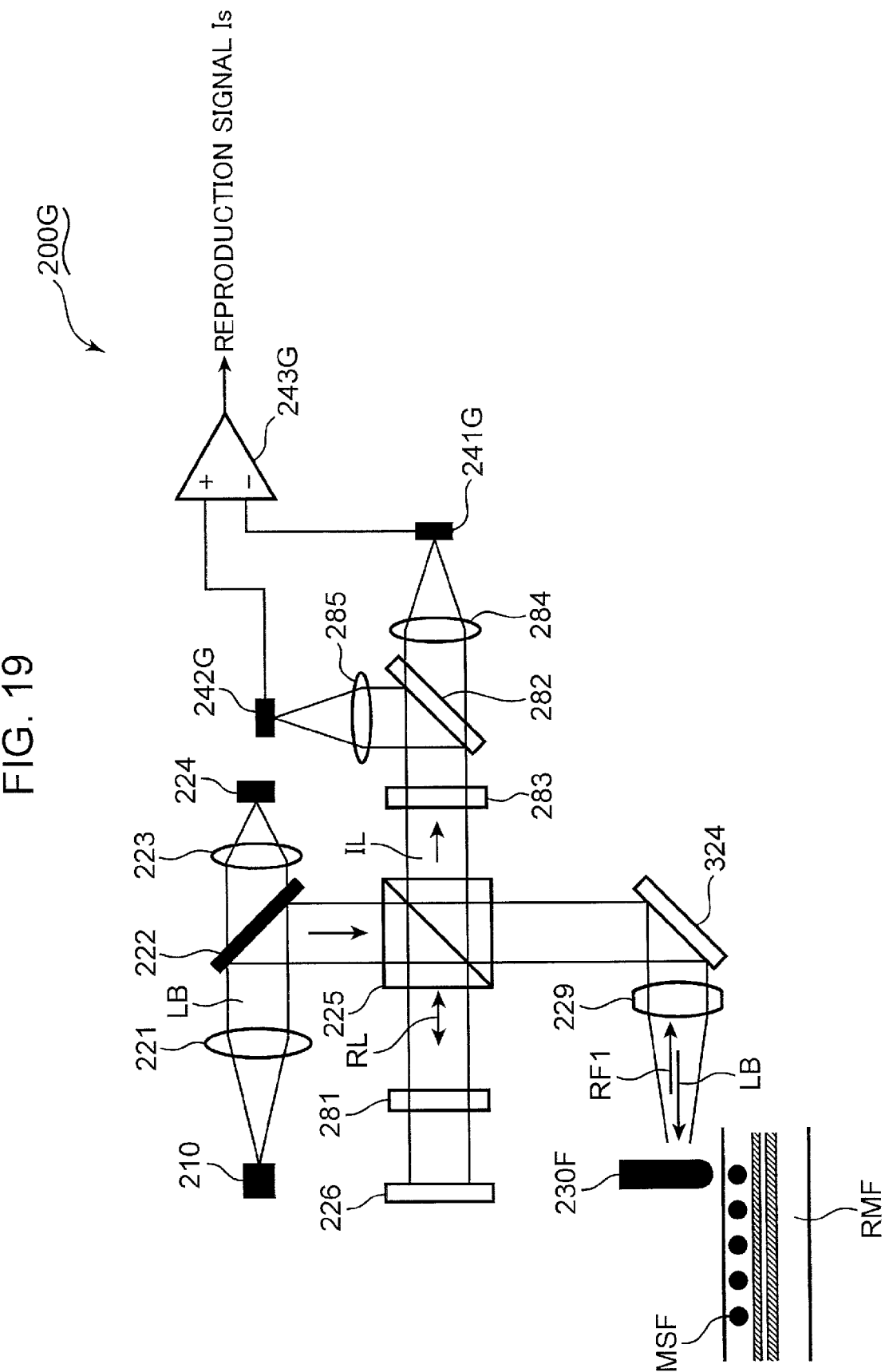
FIG. 19 is a schematic view of an optical pickup device exemplified as a detection device according to the ninth embodiment.

FIG. 19 is a schematic view of the optical pickup device 200G exemplified as the detection device. The optical pickup device 200G is designed on the basis of the principles of the detection device 100 described in the context of the first embodiment. The optical pickup device 200G is described with reference to FIG. 19. It should be noted that the same reference numerals are assigned to the same components as those described in the context of the eighth embodiment. The description in the eighth embodiment is applicable to the components, to which the same reference numerals are assigned.

The detection techniques described in the context of the eighth embodiment may achieve higher signal detection sensitivity than conventional detection techniques. However, the detection techniques described in the context of the eighth embodiment faces problems about an increase in non-modulated light components. In other words, according to the detection techniques described in the context of the eighth embodiment, direct-current components may increase in the light components whereas an S/N ratio of signals may decrease.

The optical pickup device 200G according to this embodiment uses homodyne interferometry to generate output signals in response to the state in phase. Consequently, the optical pickup device 200G may achieve a high S/N ratio.

The optical pickup device 200G adopts signal detection techniques which apply polarization differential detection techniques. Unlike the eighth embodiment, the optical pickup device 200G may calculate the detected light from differential operations to cancel DC light components.

Like the eighth embodiment, the optical pickup device 200G includes the laser beam source 210, the collimator lens 221, the mirror 222, the condensing lens 223, the light-receiving element 224, the beam splitter 225, the mirror 226, the reflecting mirror 324, the objective lens 229 and the scattering substance 230F. The optical pickup device 200G further includes a ¼ wavelength plate 281 situated between the beam splitter 225 and the mirror 226, a polarization beam splitter 282 situated on an optical path of the interfering light IL, a ½ wavelength plate 283 situated between the beam splitter 225 and the polarization beam splitter 282, a first detection lens 284 configured to receive one of two luminous fluxes, which are generated by the polarization beam splitter 282, a second detection lens 285 configured to receive the other of the two luminous fluxes, which are generated by the polarization beam splitter 282, a first photo-detector 241G configured to receive the luminous flux, which is focused by the first detection lens 284, a second photo-detector 242G configured to receive the luminous flux, which is focused by the second detection lens 285, and an arithmetic circuit 243G configured to perform differential operations for electric signals from the first and second photo-detectors 241G, 242G.

The laser beam source 210 emits the laser beam LB toward the collimator lens 221. The collimator lens 221 converts the laser beam LB into collimated light. Subsequently, the mirror 222 reflects a part of the laser beam LB toward the beam splitter 225.

The beam splitter 225 splits a part of the laser beam LB reflected by the mirror 222 as reference light RL. The beam splitter 225 allows passage of the remaining portion of the laser beam LB. The laser beam LB passing through the beam splitter 225 is reflected toward the objective lens 229 by the reflecting mirror 324. The objective lens 229 focuses the laser beam LB on the scattering substance 230F. Consequently, localized plasmon happens to the scattering substance 230F. Accordingly, the optical electric field is intensified near the scattering substance 230F.

The scattering substance 230F reflects the laser beam LB to generate the reflected light RF1. The reflected light RF1 is converted into collimated light by the objective lens 229. Subsequently, the reflecting mirror 324 reflects the reflected light RF1 toward the beam splitter 225. As described in the context of the eighth embodiment, the intensity of the plasmon resonance at the scattering substance 230F is changed by existence of the micro structures MSF. Consequently, the light amount and phase of the reflected light RF1 are changed by the intensity of the plasmon resonance.

The reference light RL generated by the beam splitter 225 passes through the ¼ wavelength plate 281 before and after the reflection by the mirror 226. Consequently, a polarization direction of the reference light RL is rotated 90°. Subsequently, the reference light RL enters the beam splitter 225. The beam splitter 225 allows passage of the reference light RL reflected by the mirror 226. On the other hand, the reflected light RF1 after the reflection from the reflecting mirror 324 is reflected by the beam splitter 225 toward the ½ wavelength plate 283. Since both of the reference light RL and the reflected light RF1 travel toward the ½ wavelength plate 283, they are multiplexed between the beam splitter 225 and the ½ wavelength plate 283 to become interfering light IL. Consequently, the polarization direction of the reflected light RF1 in the interfering light IL is orthogonal to the polarization direction of the reference light RL. In the following description, the polarization direction of the reflected light RF1 is defined as "0 degrees".

The optical axis of the ½ wavelength plate 283 is set to a direction of 22.5 degrees. Accordingly, when the interfering light IL passes through the ½ wavelength plate 283, the polarization direction of the reflected light RF1 and the reference light RL in the interfering light IL rotate 45 degrees.

The polarization beam splitter 282 emits 0-degree direction components of the reflected light RF1 and the reference light RL toward the first detection lens 284. The polarization beam splitter 282 emits 90-degree direction components of the reflected light RF1 and the reference light RL toward the second detection lens 285. Since the first detection lens 284 focuses the light toward the first photo-detector 241G, the first photo-detector 241G outputs electric signals in correspondence to the 0-degree direction light components. Since the second detection lens 285 focuses light toward the second photo-detector 242G, the second photo-detector 242G outputs electric signals in correspondence to the 90-degree direction light components. The arithmetic circuit 243G performs differential operations for the electric signals from the first and second photo-detectors 241G, 242G to output reproduction signals.

The intensity Isg of the reproduction signals is calculated from the following formula. It should be noted that the following formula is based on information from Non-Patent Document (Technical Journal of the Institute of Image Information and Television Engineers 33(1), 35-40, 2009-01-15 "Amplification of Optical Disk Signals using Homodyne Detection" Hideharu Mikami, Takahiro Kurokawa, Ken Shimano, Harukazu Miyamoto).

$$Isg = 2\eta\sqrt{I_s}\sqrt{I_r}\times\cos\phi \qquad \text{[Formula 3]}$$

"$I_s$" is intensity of the reflected light RF1. "$I_r$" is intensity of the reference light RL. "$\eta$" is conversion efficiency of the first and second photo-detectors 241G, 242G.

Under a generation condition of the plasmon resonance, a position of the mirror 226 is adjusted in advance to achieve "$\cos\phi=0$". In this case, since signal output changes from "0" at the reference time of the plasmon resonance generation, the direct-current components in the output of the reproduction signals become cancelled. Since the intensity Isg of the reproduction signals is proportional to a square root of a light amount of the reference light RL, an output variation of the reproduction signals increases as a light amount of the reference light RL becomes greater. Accordingly, the S/N ratio of the reproduction signals is improved.

Tenth Embodiment

Configuration of Optical Disk Drive Device

Figure 20:
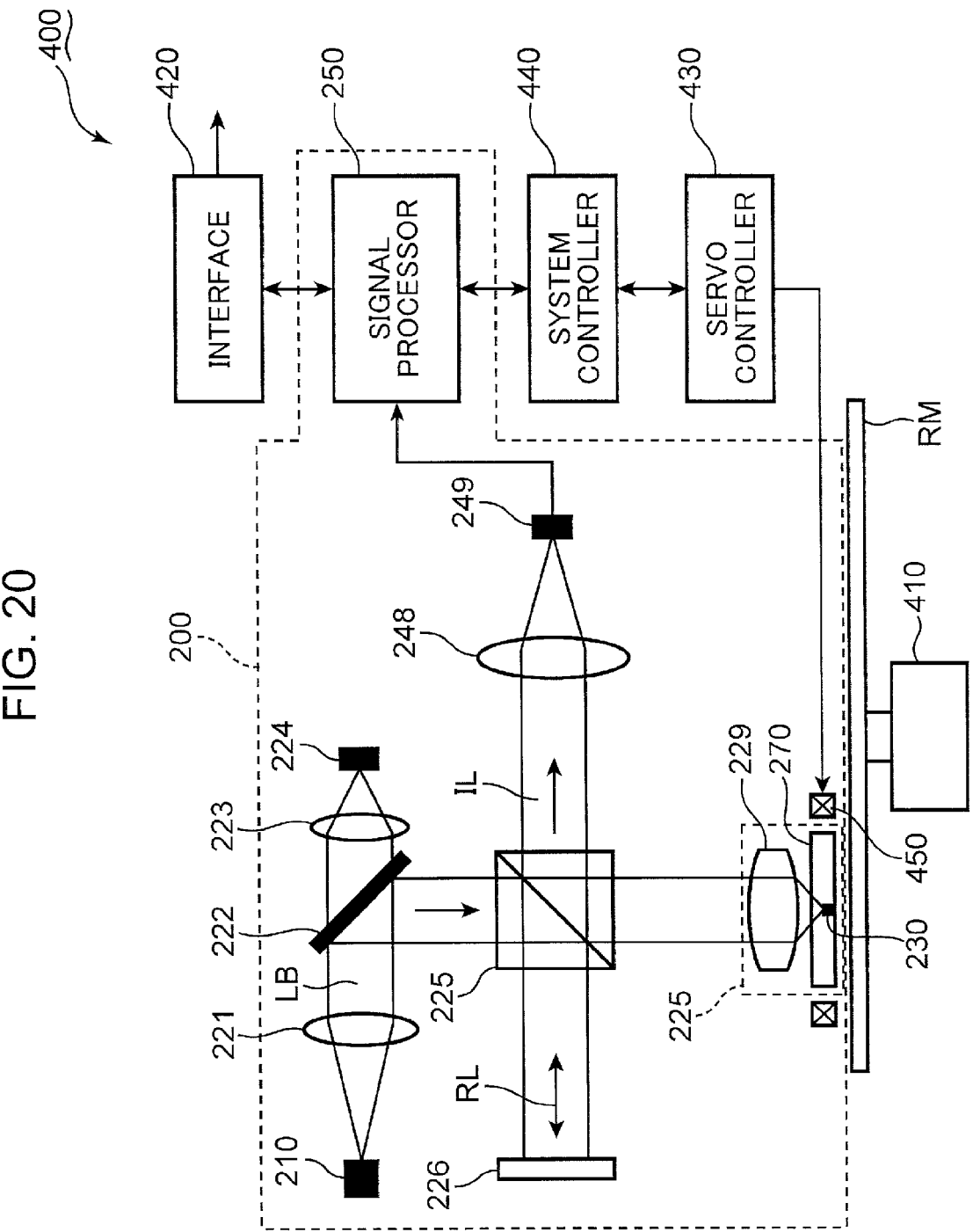
FIG. 20 is a schematic view of an optical disk drive device exemplified as a drive device according to the tenth embodiment.

FIG. 20 is a schematic view of the optical disk drive device 400 exemplified as the drive device. The optical disk drive device 400 is equipped with the optical pickup device 200 described in the context of the second embodiment. The description in the second embodiment is applicable to the optical pickup device 200.

The optical disk drive device 400 includes a spindle motor 410, a head driver (not shown), an interface 420, a servo controller 430, a feed motor (not shown), a system controller 440 and an actuator 450, in addition to the optical pickup device 200.

The servo controller 430 controls the spindle motor 410. The spindle motor 410 rotates the recording medium RM at a predetermined speed under control of the servo controller 430. In this embodiment, the spindle motor 410 is exemplified as the driver. The servo controller 430 is exemplified as the controller.

The scattering substance 230 of the optical pickup device 200 is situated near the recording medium RM rotated by the spindle motor 410. Plasmon light is generated from the scattering substance 230 positioned near the recording medium RM. The optical pickup device 200 may use the plasmon light to form a fine mark on the recording surface of the recording medium RM to record information. The optical pickup device 200 may use reflected light from the scattering substance 230 to read information signals from the recording medium RM.

The optical pickup device 200 is supported to move vertically with respect to the recording track of the recording medium RM. The optical pickup device 200 is driven by a feed motor (not shown) in the vertical direction with respect to the recording track of the recording medium RM.

The signal processor 250 performs various types of processes to signals output by the photo-detector 249 of the optical pickup device 200. The signal processor 250 may include a reproduction system for reproducing information signals read from the recording medium RM and a recording system for recording information signals. For example, the reproduction system may include a signal demodulator (not shown) and an error correction circuit (not shown). For example, the recording system may include a signal demodulator (not shown) and other circuits. The signal processor 250 configured to reproduce signals from the recording medium RM may use a signal modulator to demodulate signals (reproduction signals read from the recording medium RM) output from the photo-detector 249 of the optical pickup device 200, and then performs error correction processes by means of a correction circuit.

The interface 420 sends and receives data to and from an externally connected electronic device (e.g. a personal computer). While the optical disk drive device 400 performs the reproduction operation, the reproduction signals processed by processing elements such as a signal decoder and an error correction circuit of the signal processor 250 are sent to the externally connected electronic device via the interface 420.

The actuator 450 supports the objective lens unit 260. A biaxial actuator is exemplified as the actuator 450. The servo controller 430 servo-controls the actuator 450 and moves the objective lens unit 260 in the focusing direction and the tracking direction. In addition, the servo controller 430 may servo-control a feed motor (not shown) for feeding the optical pickup device 200. As described above, the servo controller 430 controls the spindle motor 410, which rotationally drives the recording medium RM. The servo controller 430 executes the servo control to the aforementioned various components in response to control signals from the system controller 440. The system controller 440 controls the various components of the optical disk drive device 400.

As described above, the optical disk drive device 400 may reproduce information from the recording medium RM. Meanwhile, the optical disk drive device 400 may use the optical pickup device 200 to read information from the recording medium RM rotated by the spindle motor 410 and generate reproduction signals. The optical disk drive device 400 may use a signal demodulator of the signal processor 250 to demodulate the reproduction signals, and then perform error correction processes by means of a correction circuit. After the aforementioned signal processes are performed, the reproduction signals may be sent to an externally connected electronic device through the interface 420.

As described above, the optical disk drive device 400 may record information on the recording medium RM. Meanwhile, the optical disk drive device 400 may use a signal modulator of the signal processor 250 to modulate the information signals. The optical disk drive device 400 may then generate a laser beam for recording so that the laser beam has a predetermined laser power on the basis of the modulated information signals. The optical pickup device 200 may emit the laser beam for recording toward the recording medium RM rotated by the spindle motor 410.

In this embodiment, the optical disk drive device 400 is equipped with the optical pickup device 200 described in the context of the second embodiment. Alternatively, any one of the various optical pickup devices 200D, 200E, 200F, 200G described in the context of the sixth to ninth embodiments may be used as the optical disk drive device.

Eleventh Embodiment

Configuration of Optical Disk Drive Device

Figure 21:
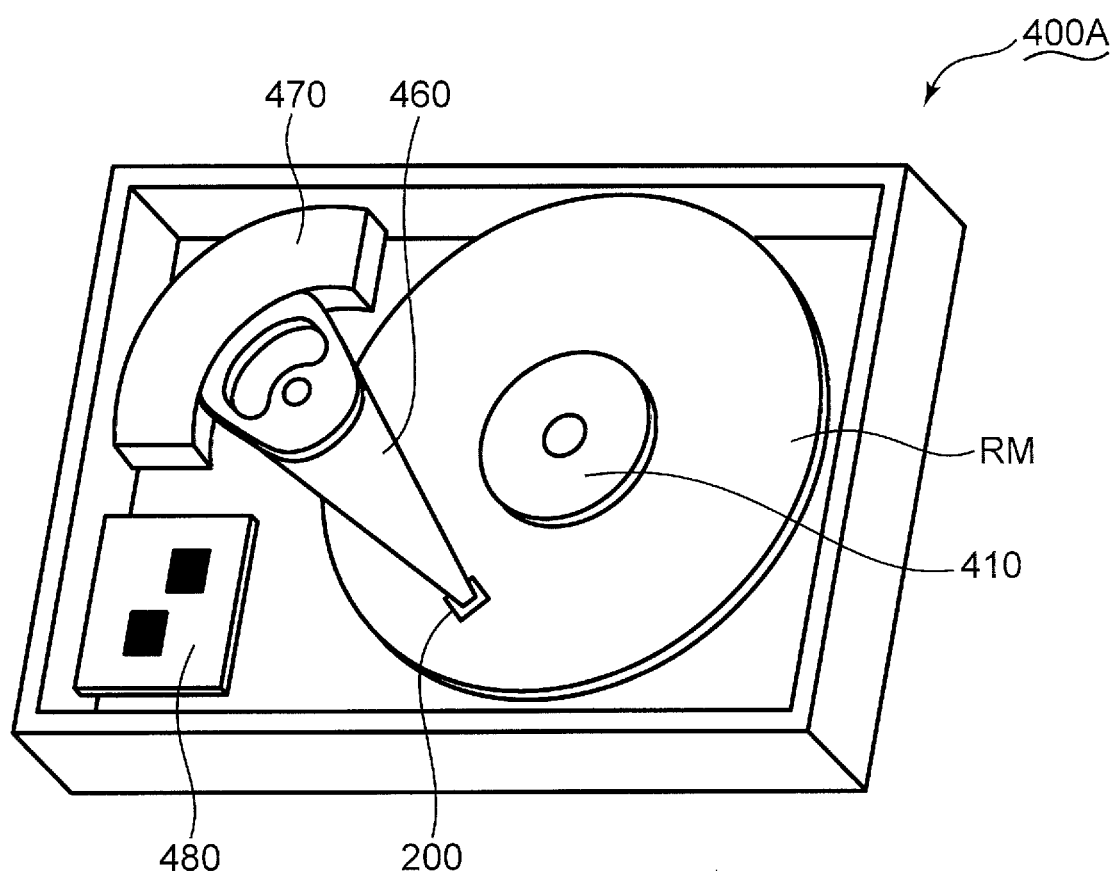
FIG. 21 is a schematic view of an optical disk drive device exemplified as a drive device according to the eleventh embodiment.

FIG. 21 is a schematic view of the optical disk drive device 400A exemplified as the drive device. The optical disk drive device 400A is equipped with the optical pickup device 200 described in the context of the second embodiment. The description in the second embodiment is applicable to the optical pickup device 200. The optical disk drive device 400A uses the spindle motor 410 described in the context of the tenth embodiment to rotate the recording medium RM. The description in the tenth embodiment is applicable to the spindle motor 410.

The optical disk drive device 400A includes a swing arm 460, a voice coil actuator 470 and a control circuit 480, in addition to the optical pickup device 200 and the spindle motor 410. As described in the context of the second embodiment, the optical pickup device 200 may not only record information on the recording medium RM but also reproduce information from the recording medium RM. The optical pickup device 200 is fixed to the swing arm 460. The voice coil actuator 470 may cause the optical pickup device 200 to seek an arbitrary position on the recording medium RM. The control circuit processes electric signals from the optical pickup device 200, and then outputs reproduction signals and control signals. The control signals may be used for controlling a position of the voice coil actuator 470.

The spindle motor 410 rotates the recording medium RM at high speed. The voice coil actuator 470 uses the swing arm 460 to move the optical pickup device 200 to an intended position on the recording medium RM. As a result of the high-speed rotation of the recording medium RM, the optical pickup device 200 floats from the recording medium RM by several nm to several ten nm. A gap interval between the optical pickup device 200 and the recording medium RM is subjected to feedback control by using an actuator (not shown) on the basis of gap error signals from the optical pickup device 200. Accordingly, the gap interval between the optical pickup device 200 and the recording medium RM is maintained to be substantially constant. A piezo-element is exemplified as the actuator used for controlling the gap interval between the optical pickup device 200 and the recording medium RM.

The optical disk drive device 400A includes one optical pickup device 200 and one recording medium RM. Alternatively, the optical disk drive device may include several recording mediums and several optical pickup devices situated in correspondence with each of the recording mediums.

In this embodiment, the optical pickup device 200 is formed integrally on the tip of the swing arm 460. Alternatively, the detection system for detecting reflected light from the laser beam source or the scattering substance may be provided to a different position.

In this embodiment, the optical disk drive device 400A is equipped with the optical pickup device 200 described in the context of the second embodiment. Alternatively, any one of the various optical pickup devices 200D, 200E, 200F, 200G described in the context of the sixth to ninth embodiments may be used as the optical disk drive device.

Twelfth Embodiment

Configuration of Optical Information Processing Apparatus

Figure 22:
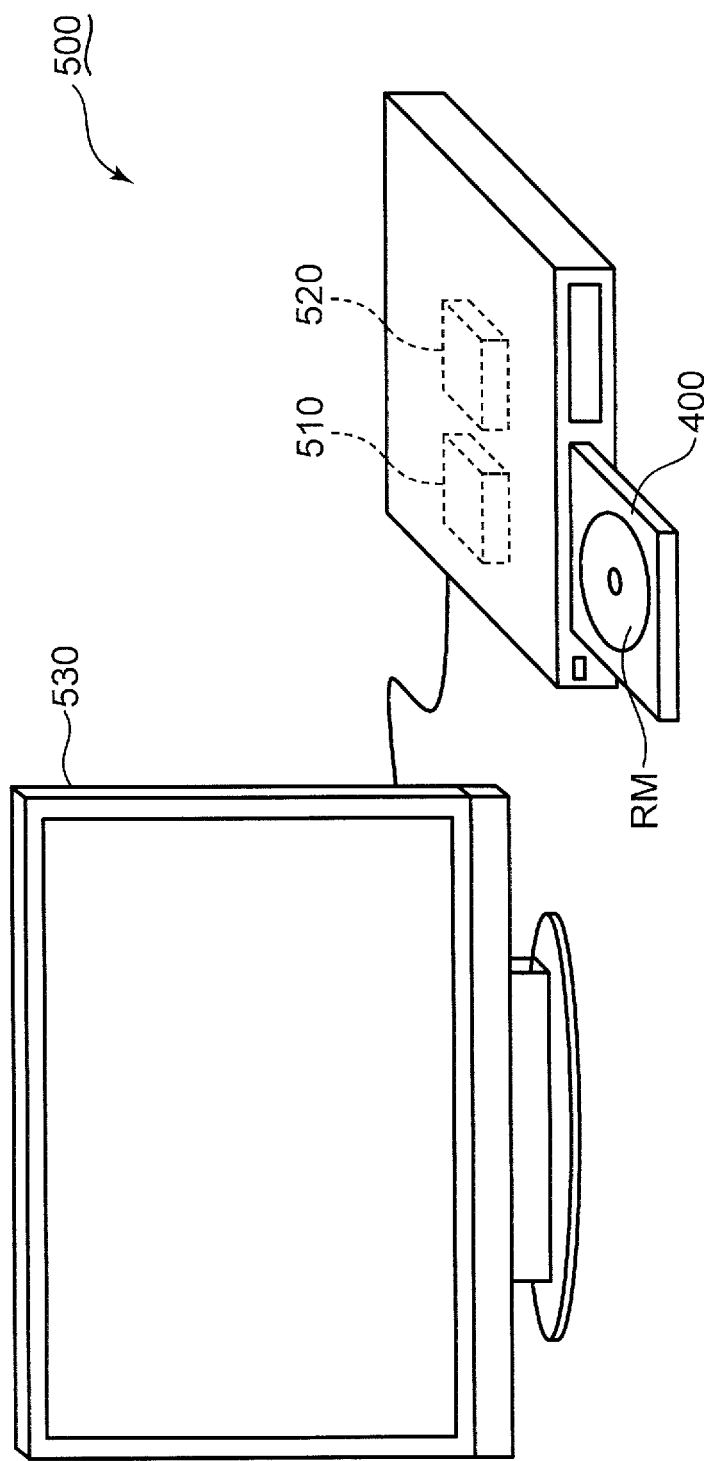
FIG. 22 is a schematic view of an exemplary optical information processing apparatus according to the twelfth embodiment.

FIG. 22 is a schematic view of the optical information processing apparatus 500. The optical information processing apparatus 500 is equipped with the optical disk drive device 400 described in the context of the tenth embodiment. The description in the tenth embodiment is applicable to the optical disk drive device 400.

The optical information processing apparatus 500 may reproduce and/or record information from and/or on the recording medium RM. The optical information processing apparatus 500 includes a recording signal processor 510 and a reproduction signal processor 520 in addition to the optical disk drive device 400. Image information is converted by the recording signal processor 510 into information signals, which are then recorded on the recording medium RM. The information signals generated by the recording signal processor 510 are recorded on the recording medium RM by the optical disk drive device 400. The reproduction signal processor 520 converts the information signals read from the recording medium RM by the optical disk drive device 400 into image information.

The optical information processing apparatus 500 may include an output device 530. For example, a CRT, an LCD and other devices configured to display image information are exemplified as the output device 530.

In this embodiment, the optical information processing apparatus 500 includes the recording signal processor 510 and the reproduction signal processor 520. Alternatively, the optical information processing apparatus may include only one of the recording signal processor and the reproduction signal processor.

In this embodiment, the optical information processing apparatus 500 includes the optical disk drive device 400. Accordingly, the optical information processing apparatus 500 may use plasmon light to record and reproduce information on and from the recording medium RM. Accordingly, the optical information processing apparatus 500 may be used for various purposes.

In this embodiment, the optical information processing apparatus 500 is equipped with the optical disk drive device 400 described in the context of the tenth embodiment. Alternatively, the optical information processing apparatus may use the optical disk drive device 400A described in the context of the eleventh embodiment.

Thirteenth Embodiment

Configuration of Information Reproduction Device

Figure 23:
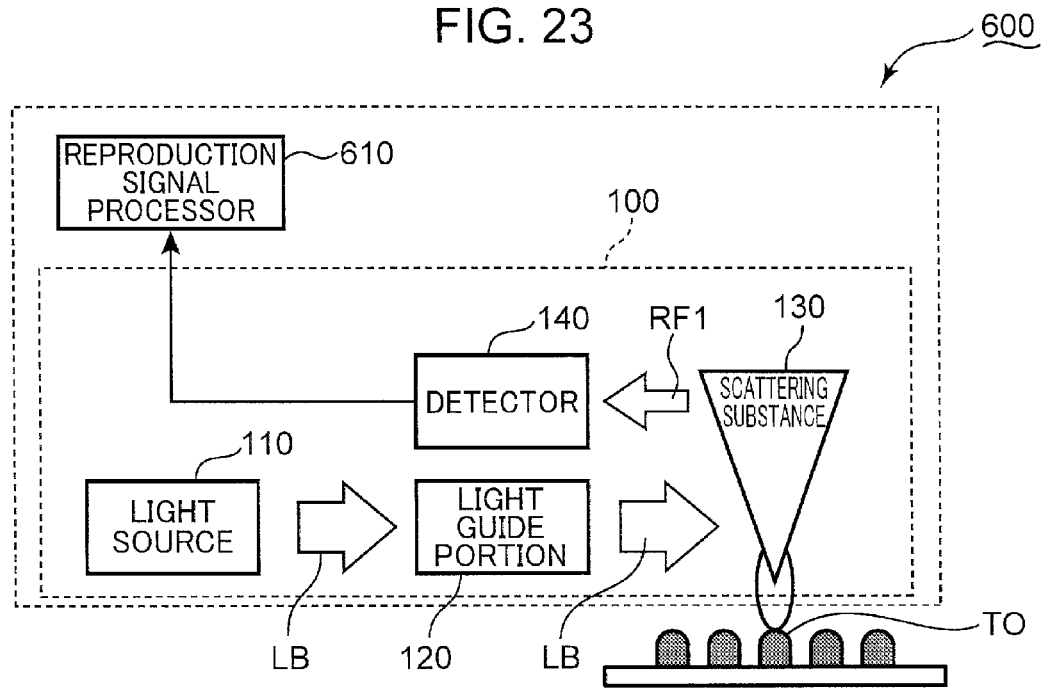
FIG. 23 is a schematic view of an exemplary information reproduction device according to the thirteenth embodiment.

FIG. 23 is a schematic view of the information reproduction device 600. The information reproduction device 600 is equipped with the detection device 100 described in the context of the first embodiment. The description in the first embodiment is applicable to the detection device 100. The various light guiding technologies described in the context of the second to ninth embodiments may be applied to the light guide portion 120 of the detection device 100. The various shapes, sizes and materials of the scattering substances described in the context of the second to ninth embodiments may be applied to the scattering substance 130. The various detection techniques described in the context of the second to ninth embodiments may be applied to the detector 140.

The information reproduction device 600 may include a reproduction signal processor 610 in addition to the detection device 100. The reproduction signal processor 610 may convert signals output from the detection device 100 into reproduction signals of a format, which allows reproduction by a predetermined output device (e.g. a CRT, an LCD or other devices configured to display image information). The information reproduction device 600 may include a drive mechanism for scanning the target object TO with plasmon light from the detection device 100.

In this embodiment, the target object TO is a recording medium on which information is recorded. The information reproduction device 600 may detect whether the target object TO (e.g. the aforementioned micro structures) is in the recorded or unrecorded state. Consequently, the information reproduction device 600 may reproduce information recorded on the recording medium.

In this embodiment, the information reproduction device 600 may use the phase change of the reflected light RF1 from the scattering substance 130 to reproduce information recorded on the recording medium with high sensitivity and little noise.

Fourteenth Embodiment

Configuration of Sensor

Figure 24:
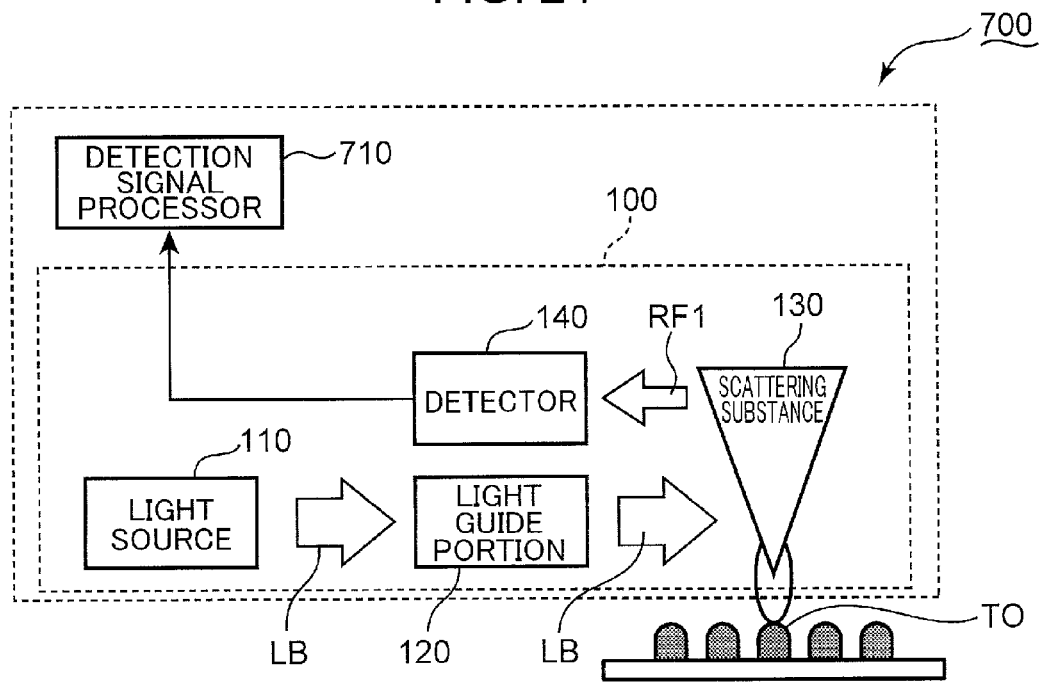
FIG. 24 is a schematic view of an exemplary sensor according to the fourteenth embodiment.

FIG. 24 is a schematic view of the sensor 700. The sensor 700 is equipped with the detection device 100 described in the context of the first embodiment. The description in the first embodiment is applicable to the detection device 100. The various light guiding technologies described in the context of the second to ninth embodiments may be applied to the light guide portion 120 of the detection device 100. The various shapes, sizes and materials of the scattering substances described in the context of the second to ninth embodiments may be applied to the scattering substance 130. The various detection techniques described in the context of the second to ninth embodiments may be applied to the detector 140.

In this embodiment, intensity of the plasmon resonance generated between the target object TO and the scattering substance 130 is changed by whether the target object TO contains specific materials. The detector 140 detects the state in phase of the reflected light RF1 from the scattering substance 130 to identify whether the target object TO contains the specific materials.

The sensor 700 includes a detection signal processor 710 in addition to the detection device 100. The detection signal processor 710 processes detection signals from the detection device 100. For example, the detection signal processor 710 may perform determination processes to determine whether the target object TO contains specific materials on the basis of the detection signals from the detection device 100. The sensor 700 may include a drive mechanism for scanning the target object TO with the plasmon light from the detection device 100.

The aforementioned specific materials may be materials in which the real part of the dielectric constant is negative. For example, Ag or compounds of Ag, and Cu or compounds of Cu may be exemplified as the specific materials.

If the target object TO contains materials in which the real part of the dielectric constant is negative, strong plasmon resonance is generated between the scattering substance 130 and the target object TO. On the other hand, the plasmon resonance generated between the scattering substance 130 and the target object TO becomes relatively weak unless the target object TO contains materials in which the real part of the dielectric constant is negative. Accordingly, intensity of the plasmon resonance is changed by whether the target object TO contains materials in which the symbol of the real part of the dielectric constant is negative. The change in the intensity of the plasmon resonance results in the change in the state in phase of the reflected light RF1 from the scattering substance 130. The sensor 700 may detect the state in phase of the reflected light RF1 from the scattering substance 130 on the basis of these relationships to determine whether the target object TO contains materials in which the symbol of the real part of the dielectric constant is negative.

In this embodiment, the sensor 700 may use the phase change of the reflected light RF1 from the scattering substance 130 to determine whether the target object TO contains materials, in which the symbol of the real part of the dielectric constant is negative, with high sensitivity and little noise.

Figure 25:
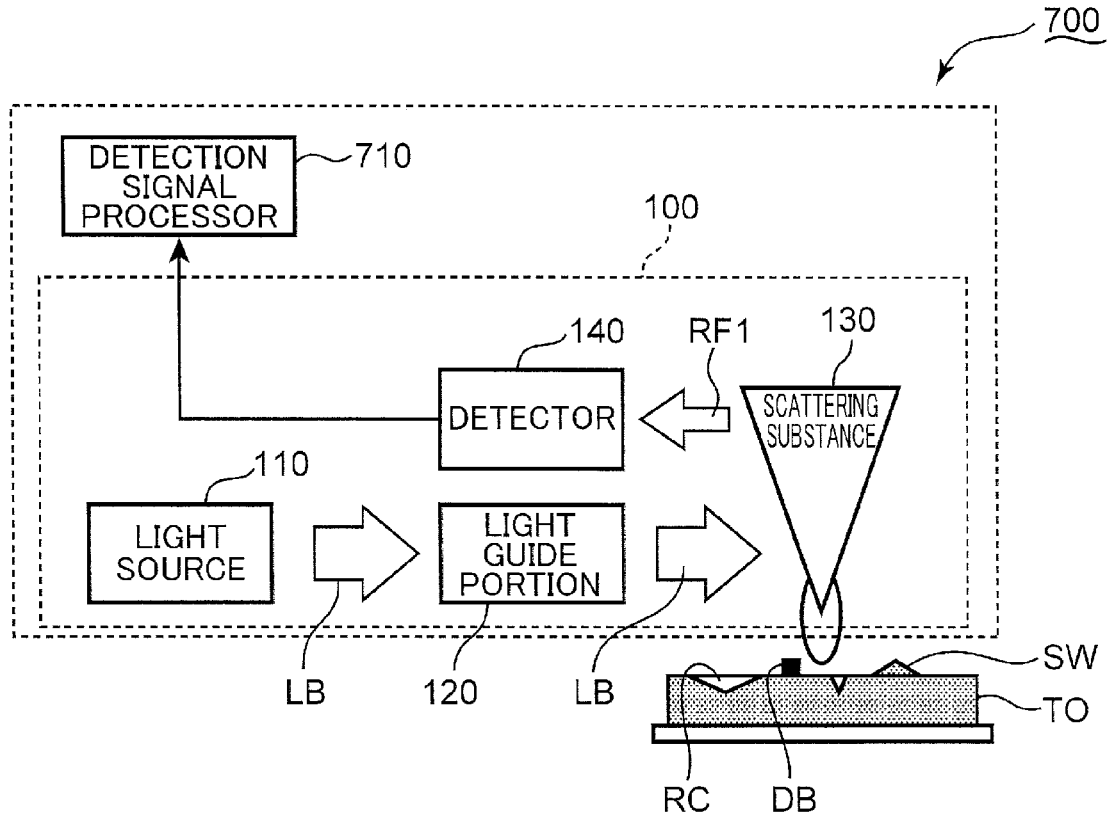
FIG. 25 is a schematic view of a sensor used for a different application from the use shown in FIG. 24.
Figure 26:
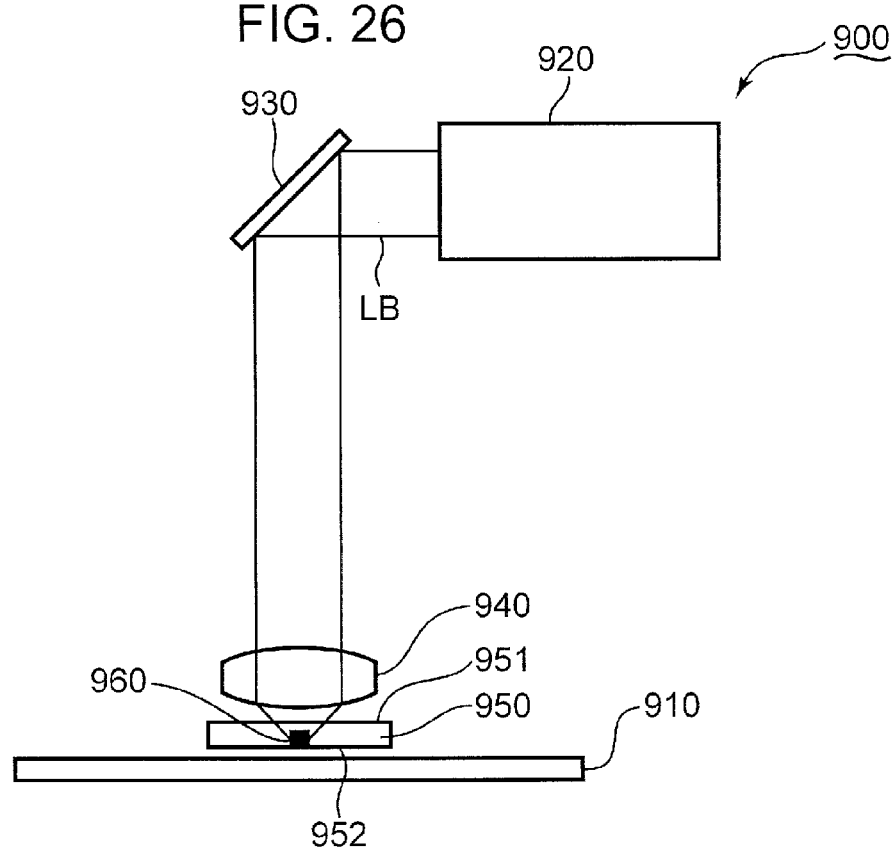
FIG. 26 is a schematic view of a conventional optical pickup device.

FIG. 25 is a schematic view of the sensor 700. Other usage of the sensor 700 is described with reference to FIG. 25.

A surface of the target object TO shown in FIG. 25 includes an area where a recess RC is formed, an area where dust DB is attached, and an area where a raised ridge SW is formed. The sensor 700 may be suitably used for detecting a shape of the target object TO.

The intensity of the plasmon resonance between the scattering substance 130 and the target object TO may be different among the area where the recess RC is formed, the area where the dust DB is attached, and the area where the raised ridge SW is formed. If there is an area formed with the recess RC near the scattering substance 130, a distance between the scattering substance 130 and the target object TO is lengthened. Consequently, intensity of the plasmon resonance decreases. On the other hand, if there is an area attached with the dust DB or an area formed with the raised ridge SW near the scattering substance 130, a distance between the scattering substance 130 and the target object TO is shortened. Consequently, the plasmon resonance is intensified.

As described above, the intensity of the plasmon resonance between the scattering substance 130 and the target object TO is changed by a shape of the target object TO. The state in phase of the reflected light RF1 from the scattering substance 130 is changed by the change in the intensity of the plasmon resonance. The sensor 700 may detect the state in phase of the reflected light RF1 from the scattering substance 130 to identify a shape of the target object TO. In the usage of the sensor 700 shown in FIG. 25, the detection signal processor 710 may perform signal processes to process detection signals from the detection device 100 in order to identify the shape of the target object TO, determination processes for determining geometrical defects of the target object TO, or other processes.

As described above, the sensor 700 may use the phase change of the reflected light RF1 from the scattering substance 130 to determine a shape of the target object TO with high sensitivity and little noise. In other words, the sensor 700 may determine with high sensitivity and little noise whether there is an area where the recess RC is formed, an area where the dust DB is attached, or an area where the raised ridge SW on the target object TO.

The various technologies described with reference to the aforementioned embodiments mainly include the following features.

The detection device according to one aspect of the aforementioned embodiments includes a light source configured to emit emission light, a scattering substance situated near a target object and configured to cause plasmon resonance between the scattering substance and the target object, a light guide portion configured to guide the emission light to the scattering substance and cause first reflected light which is reflected from the scattering substance, and a detector configured to detect a state in phase of the first reflected light.

According to the aforementioned configuration, plasmon resonance is caused between the scattering substance and the target object when the light guide portion guides the emission light from the light source to the scattering substance. Meanwhile, the scattering substance reflects the emission light to cause the first reflected light. Since the detector detects the state in phase of the first reflected light, the detection device is less susceptible to noise.

In the aforementioned configuration, the plasmon resonance may change in intensity in response to a state of the target object. The state in phase may change in response to a change in the intensity of the plasmon resonance.

According to the aforementioned configuration, the detector may accurately detect the state of the target object.

In the aforementioned configuration, the light guide portion may guide the emission light to the target object to cause second reflected light which is reflected from the target object. The detector may detect a state in phase of the second reflected light.

According to the aforementioned configuration, the light guide portion guides the emission light not only to the scattering substance but also to the target object. Consequently, the target object reflects the emission light to cause the second reflected light. Since the detector detects the state in phase of the second reflected light in addition to the first reflected light, the detector may accurately detect the state of the target object.

In the aforementioned configuration, the detection device may further include a reference light generator configured to generate reference light. The detector may include an interference optical system, which causes interference between the reference light and the first reflected light to generate interfering light, and a photo-receiver configured to detect the interfering light. The photo-receiver may generate an output signal in response to the interfering light.

According to the aforementioned configuration, the interference optical system causes interference between the reference light from the reference light generator and the first reflected light from the scattering substance to generate the interfering light. Since the photo-receiver detects the interfering light, the output signal generated by the photo-receiver is less susceptible to noise.

In the aforementioned configuration, the light guide portion may guide the emission light to the target object to cause second reflected light which is reflected from the target object. The detector may include a synthesizer, which synthesizes a synthetic wave from the first and second reflected lights, and an inclination detector configured to detect an inclination of an optical axis of the synthetic wave. The inclination detector may detect the state in phase with reference to the inclination.

According to the aforementioned configuration, the light guide portion guides the emission light not only to the scattering substance but also to the target object. Consequently, the target object reflects the emission light to cause the second reflected light. The synthetic wave is synthesized by the synthesizer from the second reflected light combined with the first reflected light from the scattering substance. The inclination detector detects the inclination of the optical axis of the synthetic wave. Since the state in phase is detected on the basis of the inclination, the detector may accurately detect the state of the target object.

In the aforementioned configuration, the target object may be a structure formed on an information recording medium. The structure becomes a recorded state under a recording operation and becomes an unrecorded state without the recording operation. The plasmon resonance may change in intensity in response to whether the structure is in the recorded or unrecorded state. The detector may detect the state in phase to identify whether the structure is in the recorded state or the unrecorded state.

According to the aforementioned configuration, since the plasmon resonance changes in intensity in response to whether the structure is in the recorded or unrecorded state, the detector may detect the state in phase to accurately identify whether the structure is in the recorded or unrecorded state.

In the aforementioned configuration, the structure may include a phase change material, which changes in phase between a crystalline state and a non-crystalline state. One of the crystalline and non-crystalline states may correspond to the recorded state whereas the other of the crystalline and non-crystalline states may correspond to the unrecorded state.

According to the aforementioned configuration, the detector may accurately identify whether the structure is in the recorded or unrecorded state on the basis of the phase change between the crystalline and non-crystalline states.

The information reproduction device according to another aspect of the aforementioned embodiments includes the aforementioned detection device. The information reproduction device uses the detection device to identify whether the structure is in the recorded or unrecorded state and reproduces information recorded on the information recording medium.

According to the aforementioned configuration, since the detection device may accurately identify whether the structure is in the recorded or unrecorded state, information recorded on the information recording medium may be accurately reproduced.

The drive device according to yet another aspect of the aforementioned embodiments includes the aforementioned detection device, a driver configured to drive an information recording medium, and a controller configured to control the driver and the detection device in response to an output signal from the detection device.

According to the aforementioned configuration, since the controller controls the driver and the detection device in response to the output signal from the detection device, the drive device may perform an accurate drive operation.

The sensor according to still another aspect of the aforementioned embodiments includes the aforementioned detection device. Intensity of the plasmon resonance is changed by whether the target object contains a specific material. The detection device detects the state in phase to identify whether the target object contains the specific material.

According to the aforementioned configuration, since the sensor includes the aforementioned detection device, it may be accurately detected whether the target object contains a specific material.

The sensor according to yet another aspect of the aforementioned embodiments includes the aforementioned detection device. The plasmon resonance changes in intensity in response to a shape of the target object. The detection device detects the state in phase to identify the shape of the target object.

According to the aforementioned configuration, since the sensor includes the aforementioned detection device, the shape of the target object may be accurately detected.

In the aforementioned configuration, the detection device may output the output signal in response to the state in phase according to homodyne interferometry.

According to the aforementioned configuration, since the detection device outputs the output signal in response to the state in phase according to homodyne interferometry, the output signal is less susceptible to a direct-current component of the detected state in phase.

The detection method according to still another aspect of the aforementioned embodiments includes steps of emitting emission light, guiding the emission light to a scattering substance situated near a target object to reflect the emission light from the scattering substance and cause first reflected light, and detecting a state in phase of the first reflected light on the basis of plasmon resonance between the target object and the scattering substance.

According to the aforementioned configuration, the scattering substance reflects the emission light to generate the first reflected light when the emission light is guided to the scattering substance situated near the target object. Subsequently, since the state in phase of the first reflected light is detected on the basis of the plasmon resonance between the target object and the scattering substance, characteristics of the target object are detected under little noise.

INDUSTRIAL APPLICABILITY

The aforementioned principles of the various embodiments may be applied to various devices which utilize detection of the state in phase of the reflected light from the scattering substance that generates plasmon light. For example, the detection of the state in phase is utilized to very accurately reproduce digital signals recorded on an information medium. Accordingly, the aforementioned principles may be suitably applied to an optical information apparatus which utilizes plasmon light to reproduce signals from an optical recording medium. The aforementioned principles may be suitably applied to a sensor in addition to an optical information apparatus. For example, the aforementioned detection of the phase state may be suitably used to determine whether target objects under inspection contain specific materials. Alternatively, the aforementioned detection of the phase state may be suitably used to detect geometry of the target object.

The invention claimed is:

1. A detection device, comprising:
a light source configured to emit emission light;
a scattering substance situated near a target object and configured to cause plasmon resonance between the scattering substance and the target object, the scattering substance moving relatively along a surface of the target object;
a light guide portion configured to guide the emission light to the scattering substance and cause first reflected light which is reflected from the scattering substance; and
a detector configured to detect a state in phase of the first reflected light,
wherein the light guide portion guides the emission light to the target object to cause second reflected light which is reflected from the target object, and
wherein the detector detects a state in phase of the second reflected light.

2. The detection device according to claim 1,
wherein the plasmon resonance changes in intensity in response to a state of the target object, and
wherein the state in phase changes in response to a change in the intensity of the plasmon resonance.

3. The detection device according to claim 1, further comprising:
a reference light generator configured to generate reference light,
wherein the detector includes an interference optical system, which causes interference between the reference light and the first reflected light to cause interfering light, and a photo-receiver configured to detect the interfering light, and
wherein the photo-receiver generates an output signal in response to the interfering light.

4. The detection device according to claim 1,
wherein the detector includes a synthesizer, which synthesizes a synthetic wave from the first reflected light and the second reflected light, and an inclination detector configured to detect an inclination of an optical axis of the synthetic wave, and
wherein the inclination detector detects the state in phase with reference to the inclination.

5. A detection device, comprising:
a light source configured to emit emission light;
a scattering substance situated near a target object and configured to cause plasmon resonance between the scattering substance and the target object;
a light guide portion configured to guide the emission light to the scattering substance and cause first reflected light which is reflected from the scattering substance; and
a detector configured to detect a state in phase of the first reflected light,
wherein the light guide portion guides the emission light to the target object to cause second reflected light which is reflected from the target object,
wherein the detector detects a state in phase of the second reflected light,
wherein the target object is a structure formed on an information recording medium,
wherein the structure is in an unrecorded state without a recording operation and is put into a recorded state by a recording operation,
wherein the plasmon resonance changes in intensity in response to whether the structure is in the recorded state or the unrecorded state, and
wherein the detector detects the state in phase to identify whether the structure is in the recorded state or the unrecorded state.

6. The detection device according to claim 5,
wherein the structure includes a phase change material, which changes in phase between a crystalline state and a non-crystalline state, and
wherein one of the crystalline state and the non-crystalline state corresponds to the recorded state whereas another of the crystalline state and the non-crystalline state corresponds to the unrecorded state.

7. An information reproduction device, comprising:
the detection device according to claim 5,
wherein the information reproduction device uses the detection device to identify whether the structure is in the recorded state or the unrecorded state, and reproduces information recorded on the information recording medium.

8. A drive device, comprising:

the detection device according to claim 1;

a driver configured to drive an information recording medium; and a controller configured to control the driver and the detection device in response to an output signal from the detection device.

9. A sensor, comprising:

the detection device according to claim 1, wherein the plasmon resonance changes in intensity in response to whether the target object contains a specific material, and wherein the detection device detects the state in phase to identify whether the target object contains the specific material.

10. A sensor, comprising:

the detection device according to claim 1, wherein the plasmon resonance changes in intensity in response to a shape of the target object, and wherein the detection device detects the state in phase to identify the shape of the target object.

11. The sensor according to claim 9, wherein the detection device outputs an output signal in response to the state in phase according to homodyne interferometry.

12. A detection method, comprising steps of:

emitting emission light;

guiding the emission light to a scattering substance situated near a target object to reflect the emission light from the scattering substance and cause first reflected light;

guiding the emission light to the target object to cause second reflected light which is reflected from the target object;

detecting a state in phase of the first reflected light and the second reflected light based on plasmon resonance between the target object and the scattering substance; and moving the scattering substance relatively along a surface of the object.

* * * * *